United States Patent
Facer et al.

(10) Patent No.: US 8,475,743 B2
(45) Date of Patent: Jul. 2, 2013

(54) MULTILEVEL MICROFLUIDIC SYSTEMS AND METHODS

(75) Inventors: Geoffrey Facer, Lane Cove (AU); Brian Fowler, San Mateo, CA (US); Emerson Cheung Quan, San Francisco, CA (US); Marc Unger, San Mateo, CA (US)

(73) Assignee: Fluidigm Corporation, South San Francisco, CA (US)

( * ) Notice: Subject to any disclaimer, the term of this patent is extended or adjusted under 35 U.S.C. 154(b) by 445 days.

(21) Appl. No.: 12/422,612

(22) Filed: Apr. 13, 2009

(65) Prior Publication Data

US 2009/0257920 A1 Oct. 15, 2009

Related U.S. Application Data

(60) Provisional application No. 61/044,417, filed on Apr. 11, 2008.

(51) Int. Cl.
| | |
|---|---|
| *B01L 3/00* | (2006.01) |
| *F16K 3/00* | (2006.01) |
| *F16K 21/20* | (2006.01) |
| *G01N 21/75* | (2006.01) |
| *F04B 19/00* | (2006.01) |
| *G05D 11/00* | (2006.01) |
| *F15C 1/14* | (2006.01) |
| *F17D 3/00* | (2006.01) |

(52) U.S. Cl.
USPC .......... 422/537; 422/502; 422/504; 422/507; 422/400; 137/3; 137/109; 137/119.06; 137/118.03; 137/597; 137/822; 137/823

(58) Field of Classification Search
USPC ............... 422/502, 100, 537, 102, 504, 507
See application file for complete search history.

(56) References Cited

U.S. PATENT DOCUMENTS

| | | | |
|---|---|---|---|
| 6,408,878 B2 * | 6/2002 | Unger et al. ............... | 137/597 |
| 6,540,895 B1 | 4/2003 | Spence et al. | |
| 6,619,311 B2 * | 9/2003 | O'Connor et al. ......... | 137/109 |
| 6,885,982 B2 | 4/2005 | Harris et al. | |

(Continued)

FOREIGN PATENT DOCUMENTS

| | | |
|---|---|---|
| CN | 1997454 B | 6/2010 |
| WO | WO 01/67369 A2 | 9/2001 |

(Continued)

OTHER PUBLICATIONS

International Application No. PCT/US2009/040104, International Search Report and Written Opinion, 10 pages, Jul. 23, 2009.

*Primary Examiner* — Bobby Ramdhanie
*Assistant Examiner* — Jennifer Wecker
(74) *Attorney, Agent, or Firm* — Kilpatrick Townsend & Stockton LLP

(57) ABSTRACT

Multilevel microfluidic devices include a control line that can simultaneously actuate valves for both sample and reagent lines. Microfluidic devices are configured to contain a first reagent in a first chamber and a second reagent in a second chamber, where either or both of the first and second reagents are contained at a desired or selected pressure. Operation of a microfluidic device includes transmitting second reagent from the second chamber to the first chamber, for mixing or contact with the first reagent. Microfluidic device features such as channels, valves, chambers, can be at least partially contained, embedded, or formed by or within one or more layers or levels of an elastomeric block.

23 Claims, 17 Drawing Sheets

U.S. PATENT DOCUMENTS

| | | |
|---|---|---|
| 6,951,632 B2 | 10/2005 | Unger et al. |
| 7,042,649 B2 | 5/2006 | Quake et al. |
| 7,059,348 B2 | 6/2006 | Nat |
| 7,062,418 B2 | 6/2006 | Lee et al. |
| 7,097,809 B2 | 8/2006 | Dam et al. |
| 7,161,736 B2 | 1/2007 | Legrand et al. |
| 7,192,629 B2 | 3/2007 | Lammertink et al. |
| 7,217,367 B2 | 5/2007 | Huang et al. |
| 7,232,109 B2 | 6/2007 | Driggs et al. |
| 7,248,413 B2 | 7/2007 | Quake et al. |
| 7,262,923 B2 | 8/2007 | Quake et al. |
| 7,279,146 B2 | 10/2007 | Nassef |
| 7,291,512 B2 | 11/2007 | Unger |
| 7,294,503 B2 | 11/2007 | Quake et al. |
| 7,318,912 B2 * | 1/2008 | Pezzuto et al. ............... 422/504 |
| 7,368,163 B2 | 5/2008 | Huang et al. |
| 7,442,556 B2 | 10/2008 | Manger et al. |
| 7,476,363 B2 | 1/2009 | Unger et al. |
| 7,526,741 B2 | 4/2009 | Lee et al. |
| 7,604,965 B2 | 10/2009 | McBride et al. |
| 7,666,361 B2 | 2/2010 | McBride et al. |
| 7,678,547 B2 | 3/2010 | Eyal et al. |
| 7,691,333 B2 | 4/2010 | McBride et al. |
| 7,749,737 B2 | 7/2010 | McBride et al. |
| 7,792,345 B2 | 9/2010 | Taylor et al. |
| 7,815,868 B1 | 10/2010 | Jones et al. |
| 7,820,427 B2 | 10/2010 | Unger et al. |
| 7,833,708 B2 | 11/2010 | Enzelberger et al. |
| 7,837,946 B2 | 11/2010 | McBride et al. |
| 8,058,630 B2 | 11/2011 | Pieprzyk et al. |
| 8,220,494 B2 * | 7/2012 | Studer et al. ............... 137/833 |
| 2002/0005493 A1 | 1/2002 | Reese et al. |
| 2002/0023684 A1 * | 2/2002 | Chow ............... 137/833 |
| 2004/0180377 A1 | 9/2004 | Manger et al. |
| 2005/0053952 A1 | 3/2005 | Hong et al. |
| 2005/0072946 A1 | 4/2005 | Studer et al. |
| 2005/0084421 A1 * | 4/2005 | Unger et al. ............... 422/100 |
| 2005/0201901 A1 | 9/2005 | Grossman et al. |
| 2005/0214173 A1 | 9/2005 | Facer et al. |
| 2005/0252773 A1 * | 11/2005 | McBride et al. ............... 204/450 |
| 2006/0172408 A1 | 8/2006 | Quake et al. |
| 2006/0188906 A1 | 8/2006 | Kim et al. |
| 2006/0233674 A1 | 10/2006 | Nelson |
| 2006/0281183 A1 | 12/2006 | Sun et al. |
| 2007/0134807 A1 | 6/2007 | Bao et al. |
| 2007/0224617 A1 | 9/2007 | Quake et al. |
| 2007/0248971 A1 | 10/2007 | Maerkl et al. |
| 2008/0029169 A1 | 2/2008 | Maerkl et al. |
| 2008/0050283 A1 | 2/2008 | Chou et al. |
| 2008/0075380 A1 | 3/2008 | Dube et al. |
| 2008/0108063 A1 | 5/2008 | Lucero et al. |
| 2008/0129736 A1 | 6/2008 | Sun et al. |
| 2008/0176211 A1 | 7/2008 | Spence et al. |
| 2008/0223721 A1 | 9/2008 | Cohen et al. |
| 2008/0230387 A1 | 9/2008 | McBride et al. |
| 2008/0264863 A1 | 10/2008 | Quake et al. |
| 2008/0274493 A1 | 11/2008 | Quake et al. |
| 2008/0281090 A1 | 11/2008 | Lee et al. |
| 2008/0292504 A1 | 11/2008 | Goodsaid et al. |
| 2009/0018195 A1 | 1/2009 | Balagadde et al. |
| 2009/0069194 A1 | 3/2009 | Ramakrishnan |
| 2009/0142236 A1 | 6/2009 | Unger et al. |
| 2009/0147918 A1 | 6/2009 | Fowler et al. |
| 2009/0168066 A1 | 7/2009 | Hansen et al. |
| 2009/0239308 A1 | 9/2009 | Dube et al. |
| 2009/0291435 A1 | 11/2009 | Unger et al. |
| 2010/0104477 A1 | 4/2010 | Liu et al. |
| 2010/0120018 A1 | 5/2010 | Quake et al. |
| 2010/0120077 A1 | 5/2010 | Daridon |
| 2010/0154890 A1 | 6/2010 | Maerkl et al. |
| 2010/0166608 A1 | 7/2010 | Quan et al. |
| 2010/0171954 A1 | 7/2010 | Quake et al. |
| 2010/0183481 A1 | 7/2010 | Facer et al. |
| 2010/0184202 A1 | 7/2010 | McBride et al. |
| 2010/0187105 A1 | 7/2010 | Unger et al. |
| 2010/0196892 A1 | 8/2010 | Quake et al. |
| 2010/0197522 A1 | 8/2010 | Liu et al. |
| 2010/0200782 A1 | 8/2010 | Unger et al. |
| 2010/0230613 A1 | 9/2010 | Pieprzyk et al. |
| 2010/0263732 A1 | 10/2010 | Hansen et al. |
| 2010/0263757 A1 | 10/2010 | Fernandes et al. |
| 2010/0311060 A1 | 12/2010 | Facer et al. |
| 2010/0320364 A1 | 12/2010 | Unger et al. |
| 2011/0002812 A1 | 1/2011 | Asogawa et al. |

FOREIGN PATENT DOCUMENTS

| | | |
|---|---|---|
| WO | WO 2007/033385 A2 | 3/2007 |
| WO | WO 2007/044091 A2 | 4/2007 |
| WO | WO 2008/043046 A2 | 4/2008 |
| WO | WO 2009/100449 A1 | 8/2009 |
| WO | WO 2010/011852 A1 | 1/2010 |
| WO | WO 2010/017210 A1 | 2/2010 |
| WO | WO 2010/077618 A1 | 7/2010 |

* cited by examiner

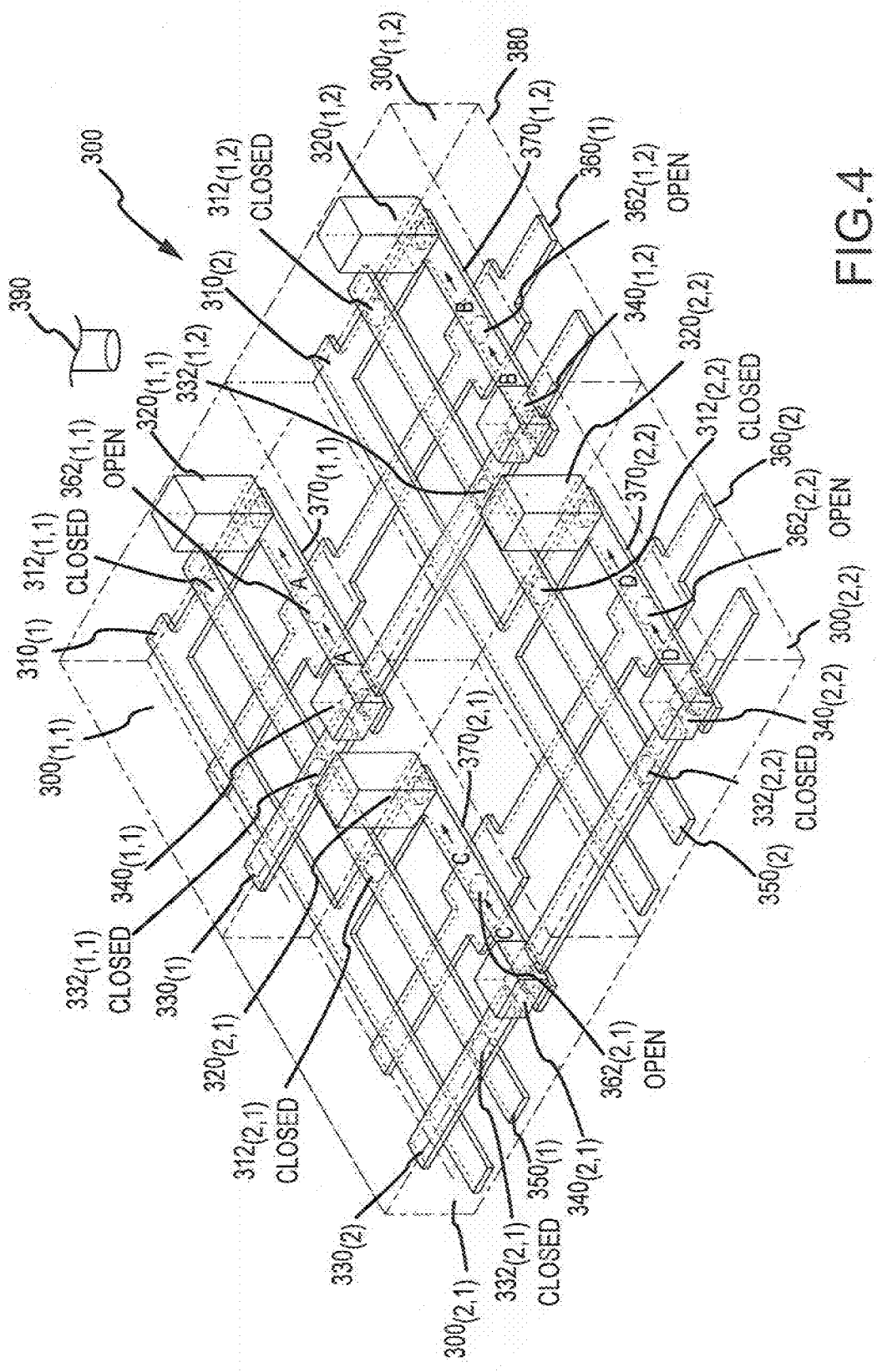

MULTILEVEL MICROFLUIDIC SYSTEMS AND METHODS

CROSS-REFERENCES TO RELATED APPLICATIONS

This application is a nonprovisional of, and claims the benefit of priority to, U.S. Patent Application No. 61/044,417, filed Apr. 11, 2008. This application is also related to U.S. patent application Ser. No. 11/043,895 filed Jan. 25, 2005. The entire content of each of the above-referenced filings is incorporated herein by reference.

BACKGROUND OF THE INVENTION

Embodiments of the present invention relate to the fields of microfluidics, lab-on-a-chip, Polymerase Chain Reactions ("PCR"), biochemical analysis, protein crystallization and screening for protein crystallization conditions, microfabrication, laboratory robotics, immunoassays, and automated biological screening and analysis, among others.

Microfluidic devices can be defined as devices having one or more fluidic pathways, often called channels, microchannels, trenches, lines, or recesses, having a cross-sectional dimension below 1000 μm and which offer benefits such as increased throughput and reduction of reaction volumes. Relatedly, there is a continuing trend toward increasing the number of reactions that can be performed with a micro fluidic device. For example, it is often desirable to provide devices having a high density of reaction chambers. Despite significant recent advances in microfluidic technology, existing fabrication techniques often present obstacles which preclude the development of even more efficient devices.

Hence, there remains a continuing need for improved manufacturing methods for producing microfluidic devices having a higher density of reaction or detection zones per unit area of the microfluidic device. At least some of these objectives will be met by embodiments of the present invention.

BRIEF SUMMARY OF THE INVENTION

Embodiments of the present invention provide microfluidic devices having a high density of reaction chambers or zones per unit area, as well as methods for their use and manufacture. Such devices can be made smaller than existing devices, and often provide improved performance characteristics. The general benefits of using microfluidic systems include a substantial reduction in time, cost, and space requirements for the devices utilized to conduct the analysis or synthesis. For example, many diagnostic assays require the use of expensive reagents, and it may be difficult or expensive to obtain large testing samples. Devices which can utilize smaller amounts of reagent and sample are able to provide more data points at a lower cost. Exemplary embodiments are well suited for use in crystal formation and amplification reactions. In some cases, microfluidic devices may have a control line that can simultaneously actuate valves for both sample and reagent lines. Relatedly, microfluidic devices may be configured to contain a first reagent in a first chamber and a second reagent in a second chamber, where either or both of the first and second reagents are contained at a desired or selected pressure. In some cases, operation of the microfluidic device includes transmitting second reagent from the second chamber to the first chamber, for mixing or contact with the first reagent. Microfluidic device features such as channels, valves, chambers, can be at least partially contained, embedded, or formed by or within one or more layers or levels of an elastomeric block.

In one aspect, embodiments of the present invention encompass microfluidic devices having a first flow channel, a second flow channel, and a control channel. The first flow channel can be formed in a first layer of an elastomeric substrate, the control channel can be formed in a second layer of an elastomeric substrate, and the second flow channel can be formed in a third layer of an elastomeric substrate. Often, the second layer is adjacent to the first layer, and the third layer is adjacent to the second layer. A change in pressure within the first control channel can modulate fluid flow within the first and second flow channels. Microfluidic devices can also include a first isolation valve disposed along the first flow channel, where the first control channel controls operation of the first isolation valve. The first isolation valve may include a deflectable membrane. Microfluidic devices can also include a second isolation valve disposed along the second flow channel, where the first control channel controls operation of the second isolation valve. The second isolation valve may include a deflectable membrane. Microfluidic devices may also include a first chamber disposed at least partially within the first layer, and a second chamber disposed at least partially within the first layer. The first chamber can be in fluid communication with the first flow channel. The second chamber can be in fluid communication with the second flow channel. In some embodiments, a change in pressure within the first control channel simultaneously modulates fluid flow within the first and second flow channels.

In another aspect, embodiments of the present invention encompass a microfluidic device having an elastomeric substrate with multiple layers. For example, the elastomeric substrate can have a first layer, a second layer, and a third layer, where the second layer is disposed between the first and third layers. The device can also include a first chamber formed at least partially within the first layer of the elastomeric substrate, and a second chamber formed at least partially within the first layer of the elastomeric substrate. Further, the device may include a first control channel formed in the second layer of the elastomeric substrate. Often, the device is configured so that a change in pressure within the first control channel modulates a first fluid flow passing through the first layer and into the first chamber, and also modulates a second fluid flow passing through the third layer and into the second chamber. In some instances, the device includes an interface channel that provides fluid communication between the first chamber and the second chamber. For example, the interface channel may be formed in the third layer. In some cases, the interface channel is in fluid communication with the second flow channel. The device may also include an interface valve disposed along the interface channel. The interface valve may modulate flow through the interface channel between the first and second chambers. In some embodiments, the interface valve comprises a deflectable membrane.

In one aspect, embodiments of the present invention provide a microfluidic device. The device can include a first flow channel formed in a first layer of an elastomeric substrate, a first chamber in fluid communication with the first flow channel, and a first isolation valve disposed along the first flow channel. The first isolation valve can include a first portion of a control channel formed in a second layer of the elastomeric substrate adjacent to the first layer. The first isolation valve can be configured to control flow through the first flow channel into the first chamber. The device may also include a second flow channel formed in a third layer of the elastomeric substrate adjacent to the second layer, a second chamber in fluid communication with the second flow channel, and a second isolation valve disposed along the second flow channel. The second isolation valve can include a second portion of the control channel formed in a second layer of the elastomeric substrate. The second isolation valve can be configured to control flow through the second flow channel into the second chamber. The device can also include a reaction channel formed in the third layer of the elastomeric substrate, in fluid communication with the first chamber and the second chamber, and an interface valve disposed along the reaction channel between the first and second chamber. The interface valve can include a portion of an interface channel formed in a fourth layer of the elastomeric substrate adjacent to the third layer, and can be configured to control flow through the reaction channel. In some embodiments, the first isolation valve includes a deflectable membrane. In some embodiments, the second isolation valve includes a deflectable membrane. In some embodiments, the interface valve includes a deflectable membrane. The first chamber can define a first chamber volume, the second chamber can define a second chamber volume. In some cases, the first chamber volume is less than the second chamber volume. In some cases, the first chamber volume is greater than the second chamber volume. In some cases, the first chamber volume is equal to the second chamber volume.

In another aspect, embodiments of the present invention encompass methods of mixing or reacting materials in a microfluidic device. An exemplary mixing technique includes flowing a first material through a first flow channel formed in a first layer of an elastomeric substrate, and flowing the first material through a first isolation valve. The first isolation valve can be disposed along the first flow channel, can include a first portion of a control channel formed in a second layer of the elastomeric substrate adjacent to the first layer, and can be configured to control flow through the first flow channel into a first chamber. The technique can also include flowing the first material from the first flow channel into the first chamber. Further, the mixing process can include flowing a second material through a second flow channel formed in a third layer of the elastomeric substrate adjacent to the second layer, and flowing the second material through a second isolation valve. The second isolation valve can be disposed along the second flow channel, can include a second portion of the control channel formed in a second layer of the elastomeric substrate, and can be configured to control flow through the second flow channel into the second chamber. The mixing procedure can also include flowing the second material from the second flow channel into the second chamber, actuating the control channel so as to inhibit flow through the first and second isolation valves, and flowing the first material from the first chamber through an interface valve into the second chamber, so as to mix the first material with the second material. The interface valve can include a portion of an interface channel formed in a fourth layer of the elastomeric substrate adjacent to the third layer, and can be configured to control flow between the first chamber and the second chamber. In some embodiments, a first isolation valve includes a first deflectable membrane, a second isolation valve includes a second deflectable membrane, and the process of actuating the control channel includes actuating the first and second deflectable membranes. In some embodiments, mixing techniques can include actuating an interface channel to provide fluid communication between the first chamber and the second chamber. An interface valve can include a portion of an interface channel formed in a fourth layer of the elastomeric substrate adjacent to the third layer, and can be configured to control flow through a reaction channel formed in the third layer. In some cases, an interface valve can include a deflectable membrane, and the process of actuating the interface channel can include actuating the deflectable membrane. Exemplary mixing techniques may also include holding the first material in the first chamber at first pressure and holding the second material in the second chamber at a second pressure, prior to flowing the first material into the second chamber. In some cases, the first pressure is greater than the second pressure. In some cases, the first pressure can be about 10 psi and the second pressure can be about 0 psi.

In yet another aspect, embodiments of the present invention include a microfluidic device having a plurality of first flow channels formed in a first layer of an elastomeric substrate, and a plurality of first chambers. Each one of the plurality of first chambers can be in fluid communication with a corresponding first flow channel of the plurality of first flow channels. A microfluidic device can also include a plurality of control channels formed in a second layer of the elastomeric substrate adjacent to the first layer, and a plurality of first isolation valves. Each one of the plurality of first isolation valves can be disposed along a corresponding first flow channel of the plurality of first flow channels, can include a first portion of a corresponding control channel of the plurality of control channels, and can be configured to control flow through the corresponding first flow channel into a corresponding first chamber of the plurality of first chambers. Further, a microfluidic device can have a plurality of second flow channels formed in a third layer of the elastomeric substrate adjacent to the second layer, and a plurality of second chambers. Each one of the plurality of second chambers can be in fluid communication with a corresponding second flow channel of the plurality of second flow channels. A microfluidic device can also have a plurality of second isolation valves. Each one of the plurality of second isolation valves can be disposed along a corresponding second flow channel of the plurality of second flow channels, can include a second portion of the corresponding control channel of the plurality of control channels, and can be configured to control flow through the corresponding second flow channel into a corresponding second chamber of the plurality of second chambers. Still further, a microfluidic device can have a plurality of reaction channels formed in the third layer of the elastomeric substrate. Each one of the plurality of reaction channels can be in fluid communication with a corresponding first chamber of the plurality of first chambers and a corresponding second chamber of the plurality of second chambers. A microfluidic device may also include a plurality of interface valves. Each one of the plurality of interface valves can be disposed along a corresponding reaction channel of the plurality of reaction channels between the corresponding first chamber and the corresponding second chamber, can include a portion of a corresponding interface channel of a plurality of interface channels formed in a fourth layer of the elastomeric substrate adjacent to the third layer, and can be configured to control flow through the corresponding reaction channel.

In a still further aspect, embodiments of the present invention encompass a microfluidic device having a first flow channel formed in a first layer of an elastomeric substrate, a first control channel formed in a second layer of an elastomeric substrate, and a second flow channel formed in a third layer of an elastomeric substrate. The second layer can be adjacent to and between the first layer and the third layer. The microfluidic device can be configured so that a change in pressure within the first control channel simultaneously modulates fluid flow within the first and second flow channels.

For a fuller understanding of the nature and advantages of the present invention, reference should be had to the ensuing detailed description taken in conjunction with the accompanying drawings.

BRIEF DESCRIPTION OF THE DRAWINGS

FIG. 4 illustrates a perspective view of a microfluidic device matrix having multiple unit cells according to embodiments of the present invention.

DETAILED DESCRIPTION OF THE INVENTION

Figure 1:
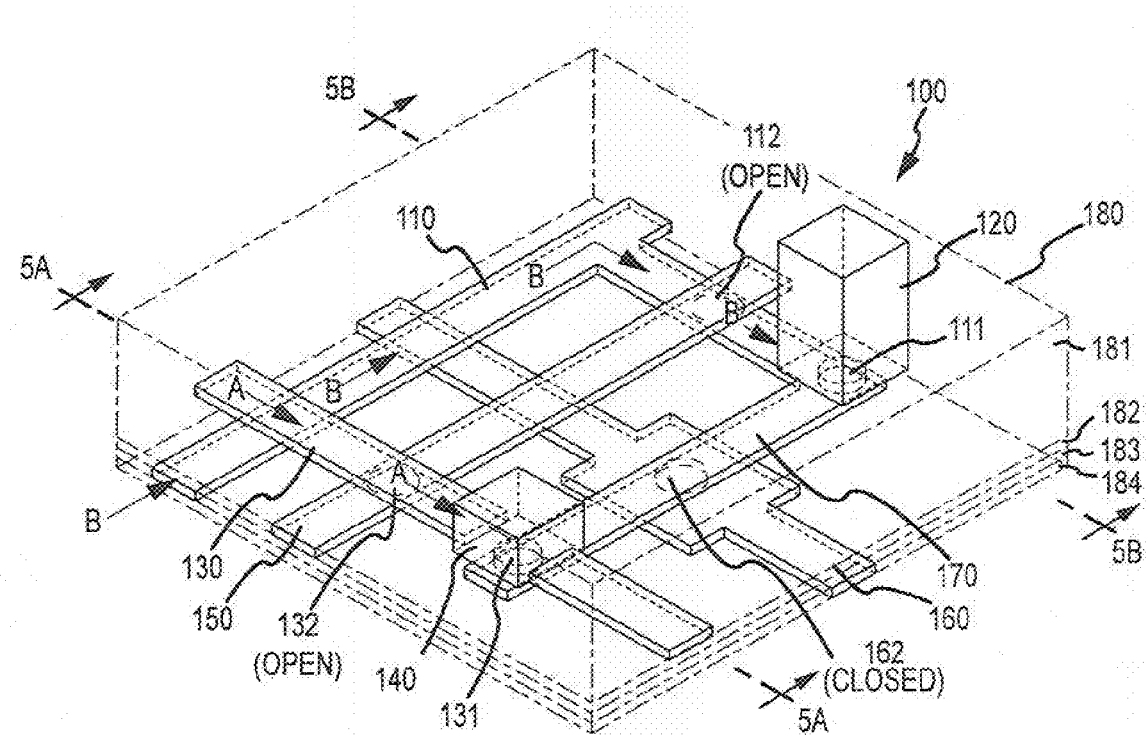
FIG. 1 depicts a perspective view of a unit cell of a microfluidic device according to embodiments of the present invention.

It is understood that the invention is not limited to the particular methodology, protocols, and reagents, etc., described herein, as these may vary as the skilled artisan will recognize. It is also to be understood that the terminology used herein is used for the purpose of describing particular embodiments only, and is not intended to limit the scope of the invention. It is also to be noted that as used herein and in the appended claims, the singular forms "a," "an," and "the" include the plural reference unless the context clearly dictates otherwise. Thus, for example, a reference to "a cell" is a reference to one or more cells and equivalents thereof known to those skilled in the art.

Unless defined otherwise, all technical and scientific terms used herein have the same meanings as commonly understood by one of ordinary skill in the art to which the invention pertains. The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law. Moreover, it is noted that like reference numerals reference similar parts throughout the several views of the drawings.

Accordingly, provided immediately below is a "Definition" section, where certain terms related to the invention are defined specifically for clarity, but all of the definitions are consistent with how a skilled artisan would understand these terms. Particular methods, devices, and materials are described, although any methods and materials similar or equivalent to those described herein can be used in the practice or testing of the invention. All references referred to herein are incorporated by reference herein in their entirety.

DEFINITIONS

PNA is peptide nucleic acid
LNA is locked nucleic acid
DA is dynamic array
PCR is polymerase chain reaction
BSA is bovine serum albumin
FRET is fluorescence resonance energy transfer
GT is genotyping
PEG is polyethylene glycol
PLP is padlock probe The term "adjacent" as used herein, generally refers to the positioning of the primer with respect to the probe on its complementary strand of the target nucleic acid analyte. The primer and probe may be separated in a range of about 1 to about 20 nucleotides, more specifically, in a range of about 1 to about 10 nucleotides, or may directly abut one another.

The term "analyte" as used herein, generally refers to a nucleic acid molecule or mixture of nucleic acid molecules, defined infra, that is to be detected or quantified using the methods of the invention. The terms "target nucleic acid analyte" and "nucleic acid analyte" are used interchangeably with the term "analyte" for the purposes of this invention.

The terms "complementary" or "complementarity" as used herein, may include the natural binding of polynucleotides under permissive salt and temperature conditions by base-pairing. For example, the sequence "A-G-T" binds to the complementary sequence "T-C-A." Complementarity between two single-stranded molecules may be "partial," in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of molecules.

The term "covalently attached" as used herein, generally refers to an attachment of one molecular moiety to another molecular moiety through covalent chemical bonds.

The term "dye" as used herein, generally refers to any organic or inorganic molecule that absorbs electromagnetic radiation at a wavelength greater than or equal 340 nm.

The term "fluorescent dye" as used herein, generally refers to any dye that emits electromagnetic radiation of longer wavelength by a fluorescent mechanism upon irradiation by a source of electromagnetic radiation, such as a lamp, a photodiode, or a laser.

The term "GT sample buffer," as used herein generally refers to a buffer that is capable of blocking binding sites on the surface of the reaction channels and chambers in a DA chip. The buffer protects the reaction components from depletion during the chip loading process or reaction. It may also reduce the usage of additional Taq-Gold Polymerase by less than about 80% for reagent costs. A 20×GT buffer may include a combination of betaine (FW 117.15), BSA, Superblock® T20 (in PBS) (Thermo Scientific, Rockford, Ill.), Superblock® (in PBS) (Thermo Scientific, Rockford, Ill.), Superblock® (in TBS) (Thermo Scientific, Rockford, Ill.), Superblock® T20 (in TBS) (Thermo Scientific, Rockford, Ill.), glycerol, PEG 20,000, PEG MME550, PEG MME5000, and Tween 20.

The term "homogenous assay" as used herein, generally refers to a method to detect or quantify a nucleic acid analyte that requires no post-assay processing to record the result of the assay. The homogenous assays may be carried out in closed tubes or microfluidic arrays where no further addition of reagents or supplementary chemicals are necessary to record the result once the assay is started. Homogenous assays allow recordation of the result of the assay in real time, meaning that the result of the assay can be continuously recorded as the assay progresses in time.

The term "hydrolysis probes" as used herein are generally described in U.S. Pat. No. 5,210,015 incorporated herein by reference in its entirety. Hydrolysis probes take advantage of the 5'-nuclease activity present in the thermostable Taq polymerase enzyme used in the PCR reaction (TaqMan® probe technology, Applied Biosystems, Foster City Calif.). The hydrolysis probe is labeled with a fluorescent detector dye such as fluorescin, and an acceptor dye or quencher. In general, the fluorescent dye is covalently attached to the 5' end of the probe and the quencher is attached to the 3' end of the probe, and when the probe is intact, the fluorescence of the detector dye is quenched by fluorescence resonance energy transfer (FRET). The probe may anneal downstream of one of the primers that defines one end of the amplification target site on the nucleic acid target analyte in the PCR reaction. Using the polymerase activity of the Taq enzyme, amplification of the target nucleic acid analyte is directed by one primer that is upstream of the probe and a second primer that is downstream of the probe but anneals to the opposite strand of the target nucleic acid. As the upstream primer is extended, the Taq polymerase reaches the region where the labeled probe is annealed, recognizes the probe-template hybrid as a substrate, and hydrolyzes phosphodiester bonds of the probe. The hydrolysis reaction irrevocably releases the quenching effect of the quencher dye on the reporter dye, thus resulting in increasing detector fluorescence with each successive PCR cycle. In particular, the hydrolysis probes of the invention may capable of detecting 8-mer or 9-mer motifs that are common in the human and other transcriptomes and may have a high $T_m$ of about 70° C. enabled by LNA analogs.

The term "label" as used herein refers to any atom or molecule which can be used to provide a detectable and/or quantifiable signal. In particular, the label can be attached to a nucleic acid or protein. Labels may provide signals detectable by fluorescence, radioactivity, calorimetric, X-ray diffraction or absorption, magnetism, enzymatic activity, and the like.

The term "nucleic acid" as used herein generally refers to cDNA, DNA, RNA, single-stranded or double-stranded and any chemical modification thereof, such as PNA and LNA. LNAs are described in U.S. Pat. Nos. 6,794,499, 6,670,461, 6,262,490, and 6,770,748 herein incorporated by reference in their entirety. Nucleic acids may be of any size. Nucleic acid modifications may include addition of chemical groups that incorporate additional charge, polarizability, hydrogen bonding, electrostatic interaction, and functionality to the individual nucleic acid bases or to the nucleic acid as a whole. Such modifications may include modified bases such as 2'-position sugar modifications, 5-position pyrimidine modifications, 8-position purine modifications, modifications at cytosine exocyclic amines, substitutions of 5-bromo-uracil, backbone modifications, methylations, unusual base pairing combinations such as the isobases isocytidine and isoguanidine and the like. The nucleic acid can be derived from a completely chemical synthesis process, such as a solid phase mediated chemical synthesis, or from a biological origin, such as through isolation from almost any species that can provide nucleic acid, or from processes that involve the manipulation of nucleic acids by molecular biology tools, such as DNA replication, PCR amplification, reverse transcription, or from a combination of those processes.

The term "nucleic acid probe" as used herein is a nucleic acid that carriers at least one covalently attached dye, such as a fluorescent dye. In particular, the probe does not contain a sequence complementary to sequences used to prime the PCR reaction.

The term "padlock probe" or "PLP" as used herein, generally refers to linear oligonucleotides having a length of about 100 base pairs. The sequences at the 3' and 5' ends of the PLP are complementary to adjacent sequences in the target nucleic acid analyte. In the central, noncomplementary region of the PLP there is a "tag sequence" that may be used to identify the specific PLP. The tag sequence may be flanked by universal primer sites or unique and/or specific primer sites, which allow PCR amplification of the tag sequence. Upon hybridization to the target, the 5' and 3' ends of the PLP are brought into close proximity and may be subsequently ligated. The resulting product is a circular probe molecule catenated to the target nucleic acid analyte. The tag regions of circularized PLPs may be amplified and quantified and/or detected using TAQMAN®Real Time PCR, for example. The presence and amount of amplicon may be correlated with the presence and quantity of target sequence in the sample. For descriptions of PLPs see, e.g., Landegren et al., 2003, Padlock and proximity probes for in situ and array-based analyses: tools for the post-genomic era, *Comparative and Functional Genomics* 4:525-30; Nilsson et al., 2006, Analyzing genes using closing and replicating circles *Trends Biotechnol.* 24:83-8; Nilsson et al., 1994, Padlock probes: circularizing oligonucleotides for localized DNA detection, *Science* 265:2085-8. The above references are incorporated by reference herein in their entirety.

The term "PCR," as used herein, generally refers to a method for amplifying, detecting, or quantifying a specific region of an analyte. One skilled in the art appreciates that there are several variations on the basic PCR technique such as allele-specific PCR, assembly PCR or polymerase cycling assembly (PCA), colony PCR, helicase-dependent amplification, hot start PCR, intersequence-specific (ISSR) PCR, inverse PCR, ligation-mediated PCR, methylation-specific PCR, multiplex ligation dependent probe amplification, multiplex PCR, nested PCR, overlap-extension PCR, quantitative PCR, quantitative real-time PCR, RT-PCR, thermal asymmetric interlaces (TAIL) PCR, touchdown PCR, and PAN-AC. Additionally, one skilled in the art would understand how to practice these variations on the basic PCR technique.

The phase "preliminary amplification reaction" as used herein, generally refers to processes for preparing the sample prior to running the homogenous assay. The term "pre-amplified sample" may be used interchangeably with the phrase "preliminary amplification reaction" for the purposes of the invention herein.

The term "purification," as used herein, generally refers to any process by which proteins, polypeptides, or nucleic acids are separated from other elements or compounds on the basis of charge, molecular size, or binding affinity.

The term "quencher" as used herein, generally refers to dye that reduces the emission of fluorescence of another dye.

The term "querying" as used herein, generally refers to determining whether a target-specific probe is associated with (e.g., bound to or catenated with) the nucleic acid analyte, and optionally quantifying the amount of target-specific probe in the sample.

A "sample" as used herein, generally refers to a sample of tissue or fluid from a human or animal including, but not limited to plasma, serum, spinal fluid, lymph fluid, the external sections of the skin, respiratory, intestinal and genitourinary tracts, tears, saliva, blood cells, tumors, organs, tissue and sample of in vitro cell culture constituents. In particular, the sample may be single cells, paraffin embedded tissue samples, and needle biopsies. Moreover, a sample may include environmental samples such as lake water, and food samples.

The phrase "substantially purified," or "substantially isolated," as used herein generally includes nucleic or amino acid sequences that are removed from their natural environment, isolated or separated, and are at least about 60% free, specifically at least about 75% free, and most specifically at least about 90% free from other components with which they may be associated with, and includes recombinant or cloned nucleic acid isolates and chemically synthesized analogs or analogs biologically synthesized by systems.

Given the tremendous diversity of polymer chemistries, precursors, synthetic methods, reaction conditions, and potential additives, there are a huge number of possible elastomer systems that could be used to make elastomeric blocks, layers, membranes, microvalves, pumps, and the like. Variations in the materials used may in some cases be driven by the need for particular material properties, i.e. solvent resistance, stiffness, gas permeability, or temperature stability. There are many, many types of elastomeric polymers. A brief description of the most common classes of elastomers is presented here, with the intent of showing that even with relatively "standard" polymers, many possibilities for bonding exist. Common elastomeric polymers include polyisoprene, polybutadiene, polychloroprene, polyisobutylene, poly(styrene-butadiene-styrene), the polyurethanes, and silicones or polysiloxanes.

Polyisoprene, polybutadiene, and polychloroprene are all polymerized from diene monomers, and therefore have one double bond per monomer when polymerized. This double bond allows the polymers to be converted to elastomers by vulcanization (generally, sulfur is used to form crosslinks between the double bonds by heating). This would easily allow homogeneous multilayer soft lithography by incomplete vulcanization of the layers to be bonded; photoresist encapsulation would be possible by a similar mechanism.

Pure polyisobutylene has no double bonds, but is crosslinked to use as an elastomer by including a small amount (.about.1%) of isoprene in the polymerization. The isoprene monomers give pendant double bonds on the polyisobutylene backbone, which may then be vulcanized as above.

Poly(styrene-butadiene-styrene) is produced by living anionic polymerization (that is, there is no natural chain-terminating step in the reaction), so "live" polymer ends can exist in the cured polymer. This makes it a natural candidate for a photoresist encapsulation system (where there will be plenty of unreacted monomer in the liquid layer poured on top of the cured layer). Incomplete curing would allow homogeneous multilayer soft lithography (A to A bonding). The chemistry also facilitates making one layer with extra butadiene ("A") and coupling agent and the other layer ("B") with a butadiene deficit (for heterogeneous multilayer soft lithography). SBS is a "thermoset elastomer", meaning that above a certain temperature it melts and becomes plastic (as opposed to elastic); reducing the temperature yields the elastomer again. Thus, layers can be bonded together by heating.

Polyurethanes are produced from di-isocyanates (A-A) and di-alcohols or di-amines (B-B); since there are a large variety of di-isocyanates and di-alcohols/amines, the number of different types of polyurethanes is huge. The A vs. B nature of the polymers, however, make them useful for heterogeneous multilayer soft lithography just as RTV 615 is: by using excess A—A in one layer and excess B—B in the other layer.

Silicone polymers have great structural variety, and provide a great number of commercially available formulations. The vinyl-to-(Si—H) crosslinking of RTV 615 (which allows both heterogeneous multilayer soft lithography and photoresist encapsulation) has already been discussed, but this is only one of several crosslinking methods used in silicone polymer chemistry.

In addition to the use of the simple "pure" polymers discussed above, crosslinking agents may be added. Some agents (like the monomers bearing pendant double bonds for vulcanization) are suitable for allowing homogeneous (A to A) multilayer soft lithography or photoresist encapsulation; in such an approach the same agent is incorporated into both elastomer layers. Complementary agents (i.e. one monomer bearing a pendant double bond, and another bearing a pendant Si—H group) are suitable for heterogeneous (A to B) multilayer soft lithography. In this approach complementary agents are added to adjacent layers.

The following is a non-exclusive list of elastomeric materials which may be utilized in connection with the present invention: polyisoprene, polybutadiene, polychloroprene, polyisobutylene, poly(styrene-butadiene-styrene), the polyurethanes, and silicone polymers; or poly(bis(fluoroaLkoxy) phosphazene) (PNF, Eypel-F), poly(carborane-siloxanes) (Dexsil), poly(acrylonitrile-butadiene) (nitrile rubber), poly (1-butene), poly(chlorotrifluoroethylene-vinylidene fluoride) copolymers (Kel-F), poly(ethyl vinyl ether), poly(vinylidene fluoride), poly(vinylidene fluoride-hexafluoropropylene) copolymer (Viton), elastomeric compositions of polyvinylchloride (PVC), polysulfone, polycarbonate, polymethylmethacrylate (PMMA), and polytertrafluoroethylene (Teflon).

Allcock et al, Contemporary Polymer Chemistry, 2nd Ed. describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed. The elasticity exhibited by elastomeric materials may be characterized by a Young's modulus. Materials having a Young's modulus of between about 1 Pa to about 1 TPa, or between about 10 Pa to about 100 GPa, or between about 20 Pa to about 1 GPa, or between about 50 Pa to about 10 MPa, or between about 100 Pa to about 1 MPa are useful in accordance with embodiments of the present invention, although materials having a Young's modulus outside of these ranges could also be utilized depending upon the needs of a particular application. In some cases, materials can have a Young's modulus of about 100 MPA (megapascals) or less. In other embodiments, the Young's modulus of the material is about 75 MPA or less, about 50 MPa or less, about 25 MPa or less, about 10 MPa or less, about 8 MPa or less, about 5 MPa or less, or about 2 MPa or less.

Embodiments of the present invention provide a microfluidic device that includes features such as channels, valves, and chambers, that are at least partially contained, embedded, or formed by or within one or more layers or levels of an elastomeric block. An exemplary microfluidic device has a reagent flow channel, or reagent line, formed in a first layer of an elastomer. The reagent flow channel includes a containment valve and a chamber conduit. The microfluidic device may also have a control channel, or containment line, formed in a second layer of the elastomer adjacent to the first layer. Further, the microfluidic device may contain a sample flow channel, or sample line, formed in a third layer of the elastomer adjacent to the second layer. The sample flow channel may include a containment valve and a chamber conduit. The control channel can be in operative association with both the reagent flow channel containment valve and the sample flow channel containment valve. The microfluidic device can include a reagent chamber in fluid communication with the reagent line, and a sample chamber in fluid communication with the sample line. The reagent chamber and the sample chamber may be in fluid communication with each other by way of a reaction flow channel or reaction line, formed in the third layer of the elastomer. The reaction line may include an interface valve. The microfluidic device may also include an interface channel formed in a fourth layer of the elastomer adjacent to the third layer. The interface channel can be in operative association with the reaction flow channel interface valve.

Embodiments of the present invention also encompass methods of making and using the microfluidic devices disclosed herein. For example, operation of a microfluidic device can involve opening one or more isolation valves, closing one or more interface valves, and flowing material past the isolation valves and into one or more chambers, optionally under pressure. Techniques may also include changing the pressure in a containment line to close the isolation valves, so as to seal off the individual chambers, and changing the pressure in an interface line, so as to open an interface valve. A first material in a first chamber can flow past an open interface valve and into a second chamber, where the first material mixes or reacts with a second material contained therein.

Turning now to the drawings, FIG. 1 depicts a perspective view of a unit cell 100 of a microfluidic device, according to embodiments of the present invention. Unit cell 100 includes a first channel 130, a first isolation valve 132, a first chamber 140, a second channel 110, a second isolation valve 112, a second chamber 120, a control channel 150, an interface channel 160, an interface valve 162, and a reaction channel 170. Typically, these features are at least partially contained, embedded, or formed by or within an elastomeric block 180. As shown here, first channel 130 is at least partially disposed within a first layer 181 of elastomeric block 180. Control channel 150 is at least partially disposed within a second layer 182 of elastomeric block 180, where the second layer is adjacent to the first layer. Second channel 110 is at least partially disposed within a third layer 183 of elastomeric block 180, where the third layer is adjacent to the second layer. Interface channel 160 is at least partially disposed within a fourth layer 184 of elastomeric block 180, where the fourth layer is adjacent to the third layer.

With reference to the "A" arrows, a first material, such as an assay reagent, can flow through first channel 130, past first isolation valve 132, and into first chamber 140. Similarly, with reference to the "B" arrows, a second material, such as an assay sample, can flow through second channel 110, past second isolation valve 112, through via 111, and into second chamber 120. To allow flow into the reaction chambers 140, 120, first and second isolation valves 132, 112, respectively, are both in an open valve state. To prevent or inhibit flow between first reaction chamber 140 and second reaction chamber 120 through reaction channel 170, interface valve 162 is in a closed valve state. Under such conditions, first channel 130 is in open fluid communication with first reaction chamber 140, and second channel 110 is in fluid communication with second reaction chamber 120, whereas fluid communication between the first and second chambers is interrupted or inhibited. Reaction chamber sizes may vary. In some embodiments, the volume of second reaction chamber 120 is different or greater than the volume of first reaction chamber 140. For example, the volume of second reaction chamber 120 can be ten times greater than the volume of first reaction chamber 140. Materials can be loaded into their respective chambers under pressure. Relatedly, materials can be loaded into chambers at certain concentrations. In some cases, a reagent solution is loaded into a chamber at a 10× concentration, and is then diluted when reacted with a sample solution contained in another chamber.

After the first and second materials have been loaded into first and second reaction chambers 140, 120 respectively, the control channel 150 can be activated so as to transform each of first and second isolation valves 132, 112 from an open valve state to a closed valve state. In this way the materials can be confined, optionally under pressure, within the reaction chambers. Hence, it is understood that a single control channel, for example control channel 150, can control flow of a first material into a first reaction chamber, and can also control flow of a second material into a second reaction chamber. Operation of a single control channel can thus act to isolate a first volume of material or solution within the first chamber via actuation of the first isolation valve 132, and can also isolate a second volume of material or solution within the second chamber via actuation of the second isolation valve 112. Relatedly, operation of a single control channel can cause a first deflection in a first direction at first isolation valve 132, and a second deflection in a second direction at second isolation valve 112, where first direction is opposite to second direction. For example, the deflection in the first isolation valve can be in the upward direction, and the deflection in the second isolation valve can be in the downward direction. Accordingly, control of more than one isolation valve can be effected simultaneously by operation of the single control channel. Materials can be confined within the reaction chambers under any suitable amount of pressure. In some embodiments, the pressure in the first reaction chamber 140 is different or greater than the pressure in the second reaction chamber 120. For example, a first material such as a reagent can be disposed in first reaction chamber 140 at a first pressure that is within a range from about 0 psi to about 15 psi. Relatedly, a second material such as a sample can be disposed in second reaction chamber 120 at a second pressure that is within a range from about 0 psi to about 10 psi. In some instances, material can be contained in the first reaction chamber 140 at about 10 psi, and material can be contained in the second reaction chamber 120 at about 0 psi. Often, loading of the microfluidic device involves introducing material into first channel 130 or second channel 110, or both, under pressure. A pressurizing mechanism can be used to drive materials into the chambers.

In some cases, embodiments are directed to systems and methods for conducting one or more reactions at one or more selected temperatures or ranges of temperatures over time. A microfluidic system may include a plurality of separate reaction chambers formed in a multi-layer elastomeric block. The system may also include a thermal transfer device proximal to or near at least one of the reaction chambers. The thermal transfer device can be formed to contact a thermal control source. Reagents for carrying out a desired reaction can be introduced into a microfluidic array device or matrix. The array device or matrix can be contacted with the thermal control device such that the thermal control device is in thermal communication with the thermal control source so that a temperature of the reaction in at least one of the reaction chamber is changed or controlled as a result of a change in temperature of the thermal control source. Exemplary thermal cycling techniques are discussed in U.S. Patent Publication No. 2007/0196912, the content of which is incorporated herein by reference. In some embodiments, a microfluidic device or chip can be coupled with or in operative association with an Integrated Heat Spreader (IHS). Such heating mechanisms are discussed in U.S. Pat. No. 7,307,802, the content of which is incorporated herein by reference.

Figure 1A:
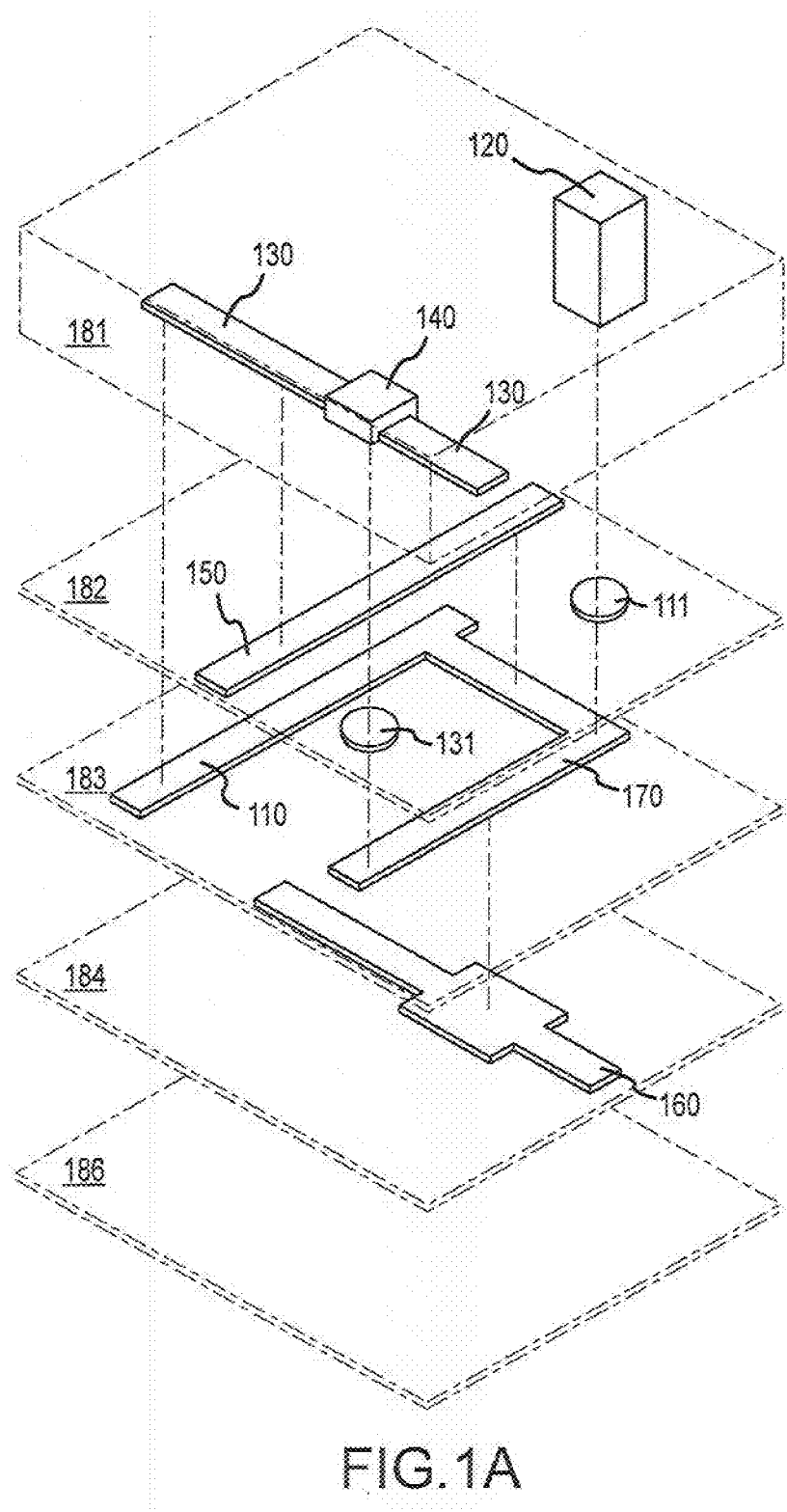
FIG. 1A shows an exploded perspective view of individual layers of a unit cell of a microfluidic device according to embodiments of the present invention.

FIG. 1A shows an exploded perspective view of individual layers of a unit cell 100 of a microfluidic device, according to embodiments of the present invention. Each layer typically includes an elastomeric membrane with one or more recesses, channels, chambers, or the like. As depicted here, first layer 181 of unit cell 100 includes a first channel 130 in fluid communication with a first chamber 140. First layer 181 also includes a second chamber 120. Second layer 182 includes a control channel 150, a first via 111, and a second via 131. Third layer 183 includes a second channel 110 and a reaction channel 170. As further discussed elsewhere herein, unit cell 100 can be configured so that second channel 110 and reaction channel 170 are in fluid communication with second chamber 120, optionally by way of via 111. For example, creating a fluid passage that extends from second channel 110 to reaction channel 170 can involve removing a portion of second layer 182 that is disposed below second chamber 120. Creation of this fluid passage can also involve removing a corresponding portion of third layer 183 that is disposed below second chamber 120. Similarly, unit cell 100 can be configured so that reaction channel 170 is in fluid communication with first chamber 140, optionally by way of via 131. For example, creating a fluid passage that extends from first channel 130 to reaction channel 170 can involve removing a portion of second layer 182 that is disposed below first chamber 140. Creation of this fluid passage can also involve removing a corresponding portion of third layer 183 that is disposed below first chamber 140. Fourth layer 184 includes an interface channel 160.

Hence, as shown here, first channel 130 is at least partially contained within a first layer 181. Control channel 150, via 111, and via 131 are each at least partially contained within a second layer 182, where the second layer is adjacent to the first layer. Second channel 110 and reaction channel 170 are at least partially contained within a third layer 183, where the third layer is adjacent to the second layer. As shown here, vias 131, 111 are disposed in second layer 182. It is understood that corresponding vias can be formed in third layer 183, so as to provide fluid communication from chamber 140 through via 131 and into channel 170, and fluid communication from chamber 120 through via 111 and into the intersection of channels 110 and 170. Interface channel 160 is at least partially contained within a fourth layer 184, where the fourth layer is adjacent to the third layer. First chamber 140 is at least partially contained within first layer 181. First chamber 140 in some instances can also be least partially contained within or in communication with passages located in second layer 182 and third layer 183, thus providing fluid communication between first chamber 140 and first channel 130, and between first chamber 140 and reaction channel 170. Second chamber 120 is at least partially contained within first layer 181. In some instances second chamber 120 can be at least partially contained within or in communication with passages located in second layer 182 and third layer 183, thus providing fluid communication between second chamber 120 and reaction channel 170.

According to the embodiment shown in FIG. 1, reaction channel 170 and interface valve 162 are not located within the same plane or level as first chamber 140 and second chamber 120. For example, reaction channel 170 is disposed in third layer 183, interface valve 162 operates at or near the boundary or junction between fourth layer 184 and third layer 183, and first and second chambers 140, 120 are disposed in first layer 181. As the routing passage or reaction channel 170 passes in a lower or different layer than that of the chambers, this allows the chambers to be located in close proximity with one another. In some embodiments, a sidewall of first chamber 140 and a facing sidewall of second chamber 120 are separated by a distance of about 120 microns. In related embodiments, a distance between facing sidewalls of first and second chambers is within a range from about 40 microns to about 225 microns. For example, a first chamber sidewall and a facing second chamber sidewall can be separated by a distance of about 50 microns, about 60 microns, about 70 microns, or about 80 microns. Often, interface valve 162 is about 50 microns in width. Hence, the distance between facing sidewalls of first and second chambers can be less than, about the same as, or more than the diameter or width of the interface valve which controls or modulates flow between the chambers. Accordingly, microfluidic devices employing such architecture can present extremely large numbers of chambers within a given area. Such high densities may be difficult to achieve in situations where a valve that controls flow between two chambers is disposed in the same layer as the chambers.

First chamber 140 can have a width within a range from about 25 microns to about 75 microns, a length within a range from about 80 microns to about 240 microns, and a height within a range from about 30 microns to about 90 microns. Relatedly, first chamber 140 can have a volume within a range from about 0.1 nanoliters to about 10 nanoliters. For example, first chamber 140 can have a width of 50 microns, a length of 162.5 microns, a height of 60 microns, and a volume of 0.49 nanoliters. Second chamber 120 can have a width within a range from about 70 microns to about 210 microns, a length within a range from about 80 microns to about 240 microns, and a height within a range from about 150 microns to about 450 microns. Relatedly, second chamber 120 can have a volume within a range from about 1 nanoliter to about 20 nanoliters. For example, second chamber 120 can have a width of 137.5 microns, a length of 162.5 microns, a height of 300 microns, and a volume of 6.7 nanoliters. A microfluidic device according to embodiments of the present invention can provide a center-to-center distance between first chamber 120 and second chamber of about 300 microns. In some cases, this center-to-center distance is within a range from about 250 microns to about 350 microns. Optionally, the center-to-center distance between the first chamber and the second chamber is about 312.5 microns.

Figure 1B:
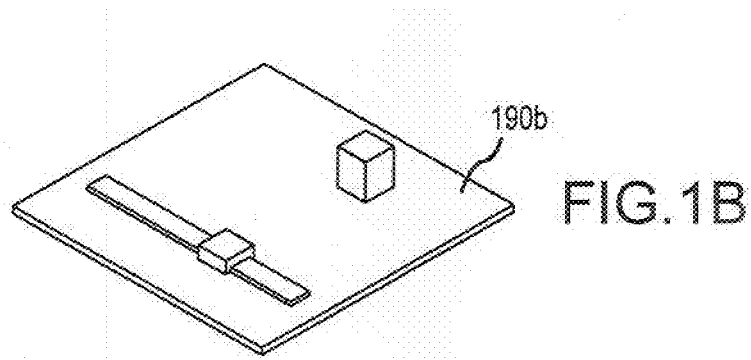
FIGS. 1B to 1E show microfluidic molds according to embodiments of the present invention.
Figure 1C:
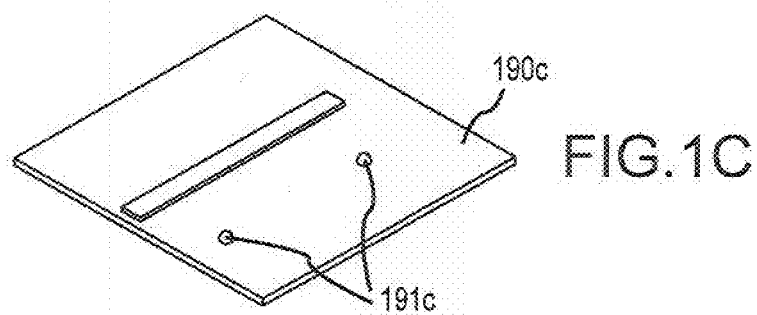
Figure 1D:
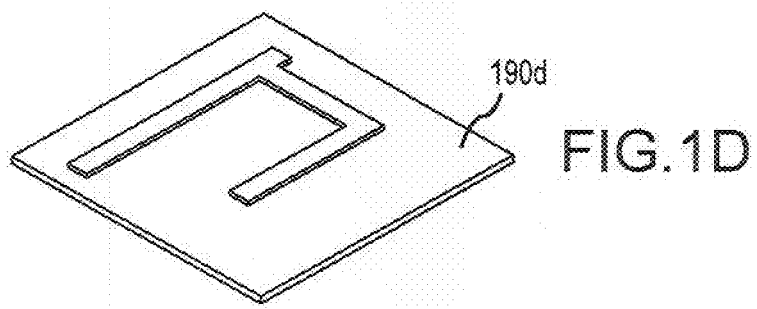
Figure 1E:
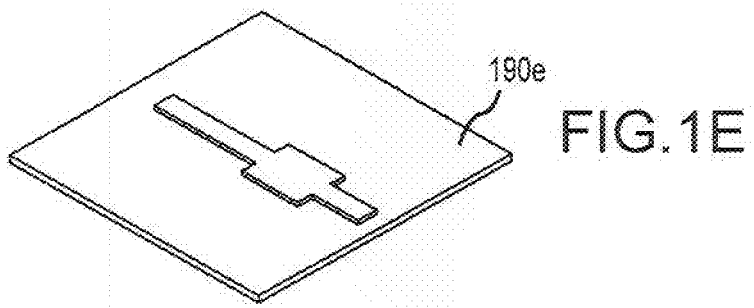

In some embodiments, a microfluidic device can include one or more layers that have been prepared according to spin or pour fabrication protocols. For example, a spin protocol can involve placing a polymeric material on a patterned disc or mold, and spinning the disc to create a layer of polymer across the disc. Exemplary polymers include polymethylmethacrylate, polystyrene, polypropylene, polyester, fluoropolymers, polytetrafluoroethylene, polycarbonate, polysilicon, and polydimethylsiloxane (PDMS). A pour protocol can involve pouring a PDMS material, for example, on a patterned template or mold, which can result in a layer of PDMS which can be peeled or pulled off the mold intact. Often, a layer prepared by a pour fabrication technique is thicker than a layer prepared by a spin fabrication technique. Elastomeric blocks can include one or more pour or spin layers, in any desired combination. In some embodiments, first layer 181 can be fabricated according to a pour protocol. For example, PDMS can be poured onto a mold that has raised portions corresponding to the various desired fluid flow channels and chambers. FIG. 1B shows an exemplary mold 190*b* which can be used to fabricate first layer 181 of FIG. 1A. After curing, the first layer can be peeled away from the mold. First layer 181 can include openings, recesses, or other voids that at least partially form or define first channel 130, first chamber 140, and second chamber 120. To create second layer 182, PDMS can be placed onto a mold that has raised portions corresponding to the various desired containment or control channels. FIG. 1C shows an exemplary mold 190*c* which can be used to fabricate second layer 182 of FIG. 1A. Mold 190*c* can also include, for example, raised or contoured portions 191*c* that form corresponding marks in second layer 182. These marks can be used during a laser ablation procedure, such that the laser ablation is directed toward the marks during the ablation. Mold 190*c* can be spun, so as to provide a thin layer of PDMS across the mold. Second layer 182 can include openings, recesses, or other voids that at least partially form or define control channel 150. In some cases, second layer 182 can be exposed to one or more laser ablations. An ablative laser beam directed to second layer 182 can form vias 111, 131. After second layer 182 is sufficiently cured, first layer 181 can be aligned and contacted with the second layer. The first layer can adhere with the second layer, and both layers can be peeled off mold 190*c* simultaneously. To create third layer 183, PDMS can be placed onto a mold that has raised portions corresponding to the various desired containment or control channels. FIG. 1D shows an exemplary mold 190*d* which can be used to fabricate third layer 183 of FIG. 1A. The mold can be spun, so as to provide a thin layer of PDMS across the mold. Third layer 183 can include openings, recesses, or other voids that at least partially form or define second channel 110 and reaction channel 170. After third layer 183 is sufficiently cured, the combined first layer 181 and second layer 182 can be aligned and contacted with the third layer. The third layer can adhere with the second layer, and all three layers can be peeled off mold 190*d* simultaneously. To create fourth layer 184, PDMS can be placed onto a mold that has raised portions corresponding to the various desired containment or control channels. FIG. 1E shows an exemplary mold 190*e* which can be used to fabricate fourth layer 184 of FIG. 1A. The mold can be spun, so as to provide a thin layer of PDMS across the mold. Fourth layer 184 can include openings, recesses, or other voids that at least partially form or define interface channel 160. After fourth layer 184 is sufficiently cured, the combined first layer 181, second layer 182, and third layer 183 can be aligned and contacted with the fourth layer. The fourth layer can adhere with the third layer, and all four layers can be peeled off mold 190*e* simultaneously. Optionally, the four layers can be placed on or contacted with a fifth layer 186 as shown in FIG. 1A. The fifth layer can include a laminate or tape, or a similarly suitable material, which operates to seal a recess in the fourth layer, so as to form or seal interface channel 160. In this way, the combined first, second, third, and fourth layers can then be placed on or contacted with the fifth layer, which may be a solid spin layer. The fifth layer can act as a sealing layer. According to some embodiments, the fifth layer may include an elastomeric material, such as PDMS. In some cases, the fifth layer can include a rigid or hard material such as glass, silicon, or a plastic such as polystyrene. The fifth layer may, for example, seal recesses formed in bottom of the fourth layer, so as to provide channels in the fourth layer. The sealing layer can include a film which may be attached to the fourth layer via an adhesive. Hence, the sealing layer can form channels from recesses molded or machined into an adjacent layer. The sealing layer can be a transparent material, for example, polystyrene, polycarbonate, or polypropylene. Relatedly, the sealing layer can be flexible, such as an adhesive tape, and may be suitable for attachment to a substrate by bonding, such as with adhesive or heat sealing, or mechanically attached such as by compression. Often, materials used to fabricate a sealing layer are compliant to form fluidic seals with each recess to form a fluidic channel with minimal leakage. A sealing layer may further be supported by an additional support layer that is rigid (not shown). In some cases, a sealing layer is rigid.

In some cases, passages or vias can be formed between channels or chambers at one layer and channels or chambers at another layer. For example, it is possible to create a via 131 through second layer 182 to provide fluid communication between first chamber 140 in first layer 181 and reaction channel 170 in third layer 183. Similarly, it is possible to create a via 111 through second layer 182 to provide fluid communication between second chamber 120 in first layer 181 and second channel 110 and reaction channel 170 in third layer 183. In some instances, creation of these vias can enlarge the volume of the reaction chambers. In some cases, the vias can be formed by using a laser punch to remove or ablate portions of elastomeric membrane. As shown in FIG. 1A, for example, reaction chambers 120, 140 can have an interior space that extends above a plane defined by the top of first channel 130. This interior space can also extend above a plane defined by the top of second channel 110, and above a plane defined by the top of reaction channel 170. Hence, during loading of the unit cell, fluid can flow through first channel 130 and upward into the interior of first chamber 140. Similarly, during loading, fluid can flow through second channel 110 and upward into the interior of second chamber 120, optionally through a via formed in the second layer.

Relatedly, during a mixing operation, fluid can flow from the interior of first chamber 140 and downward into reaction channel 170, optionally through a via 131 formed in the second layer. Similarly, during a mixing operation fluid can flow from reaction channel 170 and upward into the interior of second chamber 120, optionally through a via 111 formed in the second layer.

According to embodiments of the present invention, the second, third, fourth, and fifth layers can be processed or laser punched as part of a procedure that forms a loading passage to first channel 130 in first layer 181. Relatedly, the fourth and fifth layers can be processed or laser punched as part of a procedure that forms a loading passage to second channel 110 in third layer 183. Loading passages, vias, and the like can be formed using a drilling or ablation mechanism. For example, a loading passage or via can be fabricated by ablating a portion of the elastomeric block. Excimer lasers are well suited for such ablation techniques, as they can produce a laser beam which removes a portion of the elastomeric block. In some cases, loading passages or vias, or portions thereof, can be formed before one or more of the individual layers are adhered together. For example, a portion of a loading passage or via can be formed in a layer during the molding process, or after the molding process and before the adhesion process. Optionally, formation of at least a portion of the loading passage or via can involve etching one or more elastomeric layers prior to forming the complete multilayer elastomeric block.

Accordingly, in some embodiments fabrication methods include forming a first elastomeric layer on top of a first micromachined mold, where the first micromachined mold has one or more raised protrusions that form one or more recesses along a bottom surface of the first elastomeric layer. Methods may also include forming a second elastomeric layer on top of a second micromachined mold, where the second micromachined mold has one or more raised protrusions that form one or more recesses along a bottom surface of the second elastomeric layer. Methods may include bonding or adhering the bottom surface of the first elastomeric layer onto a top surface of the second elastomeric layer such that a channel or chamber forms in a recess between the first and second elastomeric layers. Any desired number of layers can be fabricated in this way. Methods also include positioning the last or final elastomeric layer on top of a planar substrate such that a channel or chamber forms in a recess between the final elastomeric layer and the planar substrate. Embodiments of the present invention encompass multilayer microfluidic devices having any desired elastomeric valve or pump configuration which includes such channels or chambers. Exemplary elastomeric valve and pump fabrication techniques are described in U.S. Pat. No. 6,408,878, the content of which is incorporated herein by reference.

Microfluidic device embodiments of the invention can be constructed out of any material or combination of materials that can be fabricated to have microfluidic channels and chambers, and valves that regulate flow through channels and into chambers. Materials from which a device can be fabricated include, without limitation, elastomers, silicon, glass, metal, polymer, ceramic, inorganic materials, and/or combinations of these materials.

The methods used in fabrication of a microfluidic device may vary with the materials used, and include soft lithography methods, microassembly, bulk micromachining methods, surface micro-machining methods, standard lithographic methods, wet etching, reactive ion etching, plasma etching, stereolithography and laser chemical three-dimensional writing methods, modular assembly methods, replica molding methods, injection molding methods, hot molding methods, laser ablation methods, combinations of methods, and other methods known in the art or developed in the future. A variety of exemplary fabrication methods are described in Fiorini and Chiu, 2005, "Disposable microfluidic devices: fabrication, function, and application" *Biotechniques* 38:429-46; Beebe et al., 2000, "Microfluidic tectonics: a comprehensive construction platform for microfluidic systems." *Proc. Natl. Acad. Sci. USA* 97:13488-13493; Rossier et al., 2002, "Plasma etched polymer microelectrochemical systems" *Lab Chip* 2:145-150; Becker et al., 2002, "Polymer microfluidic devices" *Talanta* 56:267-287; Becker et al., 2000, "Polymer microfabrication methods for microfluidic analytical applications" *Electrophoresis* 21:12-26; U.S. Pat. No. 6,767,706 B2, e.g., Section 6.8 "Microfabrication of a Silicon Device"; Terry et al., 1979, A Gas Chromatography Air Analyzer Fabricated on a Silicon Wafer, *IEEE Trans. on Electron Devices*, v. ED-26, pp. 1880-1886; Berg et al., 1994, *Micro Total Analysis Systems*, New York, Kluwer; Webster et al., 1996, *Monolithic Capillary Gel Electrophoresis Stage with On-Chip Detector* in International Conference On Micro Electromechanical Systems, MEMS 96, pp. 491-496; and Mastrangelo et al., 1989, *Vacuum-Sealed Silicon Micromachined Incandescent Light Source*, in Intl. Electron Devices Meeting, *IDEM* 89, pp. 503-506. Each of these references are incorporated herein by reference for all purposes.

In preferred embodiments, the device is fabricated using elastomeric materials. Fabrication methods using elastomeric materials and methods for design of devices and their components have been described in detail in the scientific and patent literature. See, e.g., Unger et al., 2000, *Science* 288: 113-16; U.S. Pat. Nos. 6,960,437 (Nucleic acid amplification utilizing microfluidic devices); 6,899,137 (Microfabricated elastomeric valve and pump systems); 6,767,706 (Integrated active flux microfluidic devices and methods); 6,752,922 (Microfluidic chromatography); 6,408,878 (Microfabricated elastomeric valve and pump systems); 6,645,432 (Microfluidic systems including three-dimensionally arrayed channel networks); U.S. Patent Application publication Nos. 2004/0115838, 2005/0072946; 2005/0000900; 2002/0127736; 2002/0109114; 2004/0115838; 2003/0138829; 2002/0164816; 2002/0127736; and 2002/0109114; PCT patent publications WO 2005/084191; WO 05030822A2; and WO 01/01025; Quake & Scherer, 2000, "From micro to nanofabrication with soft materials" Science 290: 1536-40; Xia et al., 1998, "Soft lithography" Angewandte Chemie-International Edition 37:551-575; Unger et al., 2000, "Monolithic microfabricated valves and pumps by multilayer soft lithography" *Science* 288:113-116; Thorsen et al., 2002, "Microfluidic large-scale integration" *Science* 298:580-584; Chou et al., 2000, "Microfabricated Rotary Pump" Biomedical Microdevices 3:323-330; Liu et al., 2003, "Solving the "world-to-chip" interface problem with a microfluidic matrix" *Analytical Chemistry* 75, 4718-23," Hong et al, 2004, "A nanoliter-scale nucleic acid processor with parallel architecture" *Nature Biotechnology* 22:435-39; Fiorini and Chiu, 2005, "Disposable microfluidic devices: fabrication, function, and application" Biotechniques 38:429-46; Beebe et al., 2000, "Microfluidic tectonics: a comprehensive construction platform for microfluidic systems." *Proc. Natl. Acad. Sci. USA* 97:13488-13493; Rolland et al., 2004, "Solvent-resistant photocurable "liquid Teflon" for microfluidic device fabrication" *J. Amer. Chem. Soc.* 126:2322-2323; Rossier et al., 2002, "Plasma etched polymer microelectrochemical systems" Lab Chip 2:145-150; Becker et al., 2002, "Polymer microfluidic devices" Talanta 56:267-287; Becker et al., 2000, and other references cited herein and found in the scientific and patent literature. Each of these references are incorporated herein by reference for all purposes.

Embodiments of the present invention further encompass aspects of microfluidic fabrication and production, as well as microfluidic device operation and use, as disclosed in U.S. patent application Ser. No. 12/018,138 filed Jan. 22, 2008, the content of which is incorporated herein by reference for all purposes.

Any of a variety of ablation, etching, or similar techniques can be used to form vias or passages in an elastomeric block, membrane, or layer. Such etching procedures are well suited for creating elastomeric layers having multiple holes or apertures, for example. In an exemplary process, an elastomeric material is placed on a wafer or mold, and allowed to cure. The elastomeric material can include one or more polymers incorporating materials such as chlorosilanes or methyl-, ethyl-, and phenylsilanes, and polydimethylsiloxane (PDMS) such as Dow Chemical Corp. Sylgard 182, 184 or 186, or aliphatic urethane diacrylates such as (but not limited to) Ebecryl 270 or Irr 245 from UCB Chemical may also be used. In some cases, the elastomeric material is deposited on the wafer or mold in a spin coating process, a spray coating process, a dip coating process, a screen printing process, an inkjet deposition process, or the like. The curing procedure can involve baking or room temperature vulcanizing (RTV), photocuring, and the like.

An elastomeric composition may include multiple parts, which can be mixed together at various ratios to obtain desired bond properties. For example, an elastomeric material may include a Part A and a Part B, which when mixed together in prescribed amounts facilitates the desired bond parameters. In some cases, the parts may be mixed in a ratio within a range from about 3:1 to about 30:1. For example, an elastomeric PDMS composition is baked to provide a 10:1 RTV layer.

In some cases, a photoresist material can be placed on the cured elastomeric material. For example, an SU-8 resist (available from MicroChem Corp., Newton Mass.) can be applied to the elastomer. Exemplary SU-8 resists include SU-8 2000, SU-8 3000, SU-8 2007, SU-8 3005, and the like. The photoresist can be deposited on the elastomeric material in a spin coating procedure, at a desired rotational speed and duration. In some cases, the spin coating can be performed at a rotational speed within a range from about 1000 to about 10,000 rpm, and for a duration within a range from about 20 seconds to about 2,000 seconds. For example, the spin coating can be performed at 5000 rpm for 200 seconds. Following this deposition, the photoresist mask can have a thickness or depth within a range from about 0.5 to about 50 microns. In some cases, the thickness is about 5 microns. The thickness of the mask can be selected for facile via opening formation, and the selected spin time can eliminate or inhibit beading of the photoresist material. The photoresist material can be used as an etch mask.

Additional procedures can be performed to prepare the photoresist for lithography exposure. For example, the photoresist can be processed at a selected temperature for a selected time duration. In some embodiments, the photoresist is soft baked at a temperature within a range from about 45° C. to about 85° C. Relatedly, the photoresist can be baked for a duration within a range from about 1 minute to about 10 minutes. In some cases, the soft bake is performed for 5 minutes at 65° C. Such preparation techniques can help to eliminate or inhibit photoresist mask cracking at exposure. The preparation procedure may also include cooling the photoresist. For example, the photoresist may be cooled at room temperature or at a temperature within a range from about 18° C. to about 37° C., and for a duration within a range from about 3 minutes to about 300 minutes. In some cases, the photoresist is cooled for about 30 minutes.

The lithography procedure can involve multiple exposure steps. For example, a first exposure step can be performed with a first exposure mask, and a second subsequent exposure step can be performed with a second exposure mask. An exposure step can involve the application of radiation or energy, through an exposure mask, toward a photoresist. Exposure radiation can include ultraviolet light, near ultraviolet light, deep ultraviolet light, visible light, infrared light, or energy at any desired wavelength along the electromagnetic spectrum. In some cases, exposure radiation is delivered at one or more wavelengths within a range from about 10 to about $10^{-9}$ cm. In some cases, the type of radiation or energy is selected based on the composition of the photoresist. For example, specific types of radiation or energy can be applied to I-line photoresists, G-line photoresists, H-line photoresists, and the like.

The use of multiple masks can help to prevent or inhibit the effect of contaminants on a mask from replicating on the photoresist. For example, if there is an unwanted particle on the first mask at a certain location, exposure with a second mask can help to ensure exposure of the photoresist at that location. The exposure process can be followed with a post-exposure bake (PEB) procedure. In some cases, a PEB procedure is performed for a duration within a range from about 0 to about 200 minutes, and at a temperature within a range from about 50° C. to about 80° C. For example, a PEB can be performed for 2 minutes at 65° C. In some cases, the PEB can operate to cross-link the photoresist mask material, rendering the material nonsoluble. Thereafter, the exposed photoresist can be allowed to cool. An exemplary cooling process is performed at a temperature within a range from about 18° C. to about 37° C. for a duration within a range from about 1 hour to about 40 hours. In some cases, the exposed photoresist is cooled at room temperature for about 18 hours.

A development process can be performed following exposure. In some cases, the photoresist mask is developed for a duration within a range from about 10 seconds to about 10 minutes. During the development process a developer is applied to the exposed photoresist. The developer can include, for example, an organic solvent such as acetate. It is understood that the developer or solvent may be selected based on the composition of the photoresist. The developer can operate to dissolve or degrade areas or locations of the photoresist layer that were unexposed or masked during the exposure process. Following development, the photoresist mask is subject to a drying procedure. For example, the mask can be spin-dried. The mask may also be allowed to relax for a desired period of time. In some cases, the mask is allowed to relax at or near room temperature for a duration within a range from about 1 minute to about 48 hours.

Optionally, additional elastomeric layers can be spin-coated or otherwise applied onto the developed photoresist. For example, an RTV coating have a thickness or depth within a range from about 0.3 microns to about 30 microns can be deposited on the photoresist mask. The elastomeric coating can be baked for a duration within a range from about 5 minutes to about 3 hours, at a temperature within a range from about 40° C. to about 80° C. In some cases, a 3 micron RTV coating is spin-coated on an SU-8 mask, and baked for 1 hour at 60° C. Such techniques can help to minimize lateral etch, and reduce via size non-uniformity. The RTV layer can be deposited on a patterned photoresist layer, to help prevent or inhibit the formation of pinholes in the underlying elastomer.

Typically, etching involves removing certain areas of the elastomeric material that are not protected by the photoresist following development. In an exemplary procedure, etching can be performed for a duration within a range from about 1 minute to about 20 minutes and at a temperature within a range from about 50° C. to about 90° C. For example, etching can be carried out in an 80% tetrabutylammonium fluoride (TBAF) etchant solution for 6-8 minutes at 70 degrees ° C. In some cases, etching is performed in an ultrasonic bath tank, optionally in degas mode. Such procedures can help to ensure a uniform etching depth, with minimum damage to a photoresist mask during the etching procedure. Etching can be followed with a deionized water wash. In some cases, a hot water wash is performed for three minutes. The photoresist mask can be removed with adhesive tape. A deionized water wash can be applied again, optionally for 3 minutes. Stacking procedures can provide additional layers to the elastomer. In some cases, adjacent layers adhere to one another by way of interlayer bonding.

Figure 2:
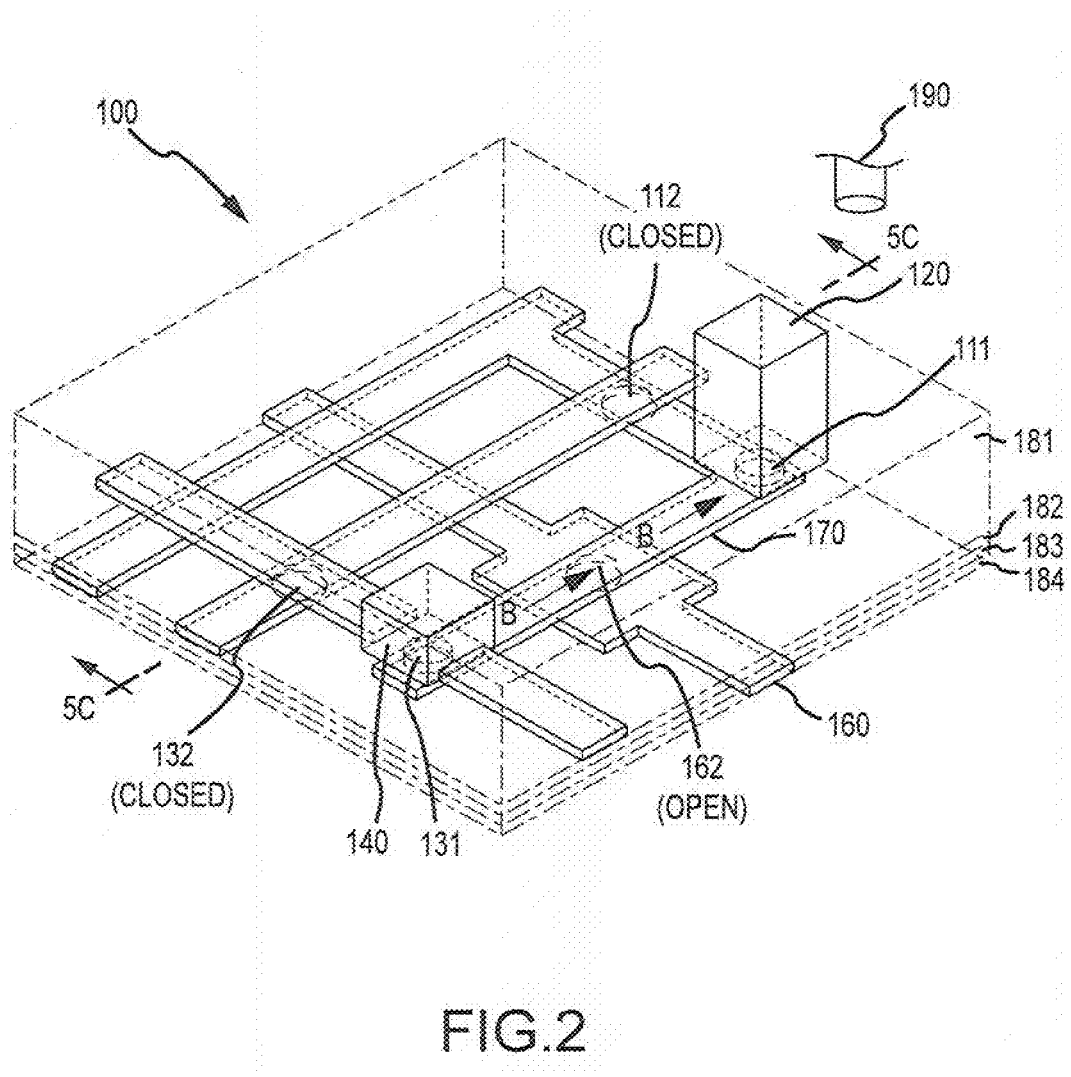
FIG. 2 illustrates a perspective view of unit cell of a microfluidic device according to embodiments of the present invention.

FIG. 2 illustrates another perspective view of unit cell 100. As shown here with reference to the "A" arrows, the first material can flow from first reaction chamber 140, through via 131, through reaction channel 170, past interface valve 162, through via 111, and into second reaction chamber 120, where the first material can contact the second material. It is understood that in some embodiments, the second material can flow from second reaction chamber 120, through via 111, through reaction channel 170, past interface valve 162, through via 131, and into first reaction chamber. To allow such flow through reaction channel 170, the interface channel 160 can be activated so as to transform interface valve 162 from a closed valve state to an open valve state. Under such conditions, the first and second reaction chambers 140, 120 are in open fluid communication by way of the reaction channel and the vias. When, for example, material contained in first reaction chamber 140 is more highly pressurized relative to material contained in second reaction chamber 120, the pressure differential can help to release or open interface valve 162. Relatedly, such a pressure differential can facilitate mixing between the first material and the second material, as the first material is forcefully expelled from first chamber and into second chamber, thus squirting a stream of first material into a second material contained in the second chamber, where the first material can diffuse into or permeate through the second material. Often, the presence, absence, or extent of any reaction between the first and second materials, or involving either or both of the first and second materials, within the second reaction chamber can be characterized, confirmed, detected, or quantified by inspection, for example with a reader, sensor, or imaging device 190. An imaging device 190 can include a camera, optionally having a charge-coupled device (CCD), that detects or monitors energy that emits from the chamber. In some cases, the imaging device can detect emission intensity output. Exemplary imaging devices and reader techniques suitable for use with embodiments of the present invention are described in U.S. Pat. No. 7,307,802 issued Dec. 11, 2007, the content of which is incorporated herein by reference. In some cases, a reaction within a chamber is facilitated by a thermal cycler. Embodiments of the present invention encompass systems and methods for mixing or reacting materials within chambers, where such mixing or reacting procedures involve any of a variety of desired thermal cycling heating protocols or thermal gradient modalities.

Figure 3:
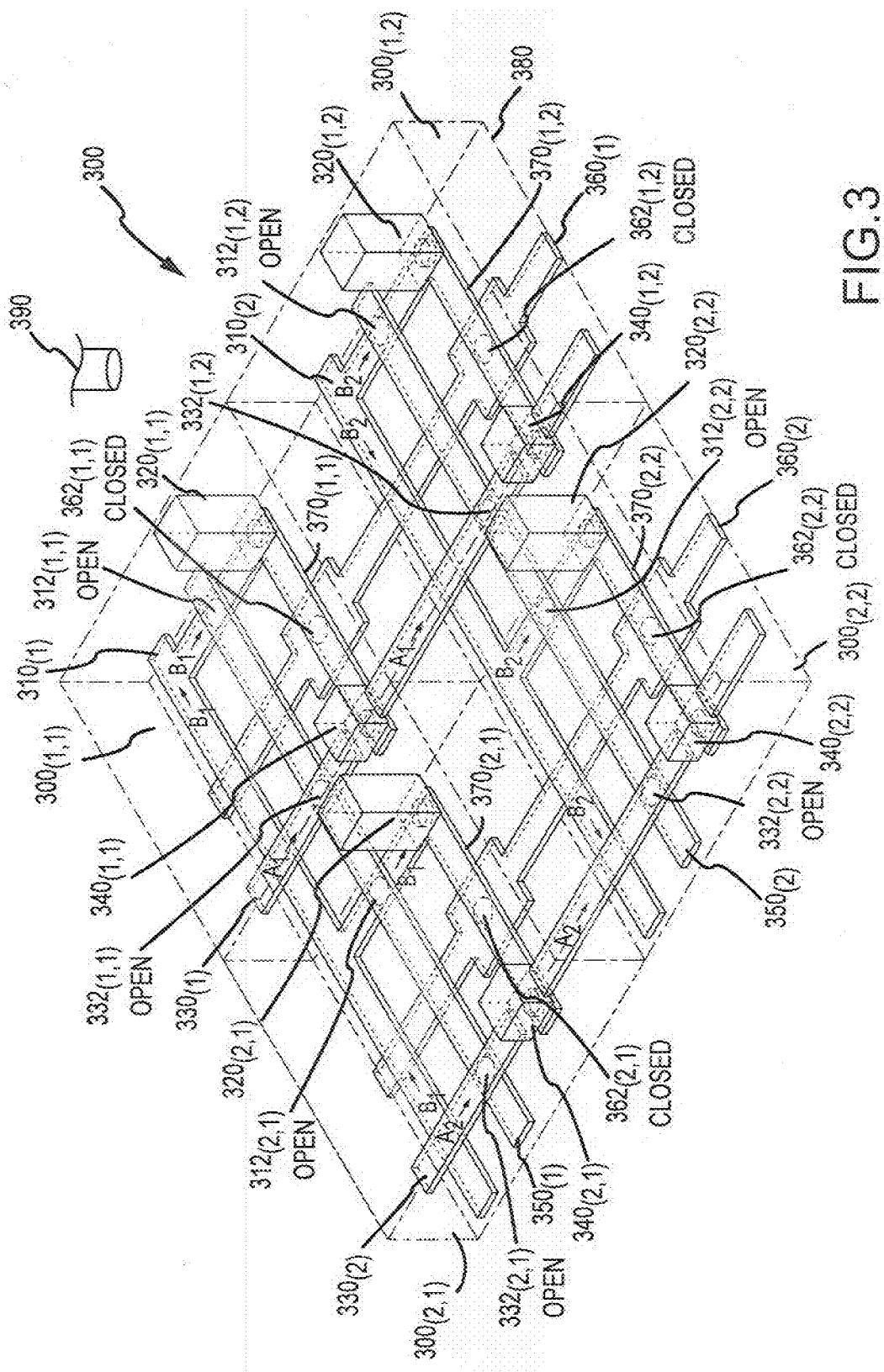
FIG. 3 illustrates a perspective view of a microfluidic device matrix having multiple unit cells according to embodiments of the present invention.

FIG. 3 illustrates a perspective view of a matrix 300 having four unit cells $300_{(1,1)}$, $300_{(1,2)}$, $300_{(2,1)}$, and $300_{(2,2)}$ arranged in two rows and two columns. Matrix 300 includes a plurality of first channels $330_{(1)}$, $330_{(2)}$, a plurality of first isolation valves $332_{(1,1)}$, $332_{(1,2)}$, $332_{(2,1)}$, $332_{(2,2)}$, a plurality of first chambers $340_{(1,1)}$, $340_{(1,2)}$, $340_{(2,1)}$, $340_{(2,2)}$, a plurality of second channels $310_{(1)}$, $310_{(2)}$, a plurality of second isolation valves $312_{(1,1)}$, $312_{(1,2)}$, $312_{(2,1)}$, $312_{(2,2)}$, a plurality of second chambers $320_{(1,1)}$, $320_{(1,2)}$, $320_{(2,1)}$, $320_{(2,2)}$, a plurality of control channels $350_{(1)}$, $350_{(2)}$, a plurality of interface channels $360_{(1)}$, $360_{(2)}$, and a plurality of reaction channels $370_{(1,1)}$, $370_{(1,2)}$, $370_{(2,1)}$, $370_{(2,2)}$. It is appreciated that the unit cell architecture embodiments disclosed herein can be scaled to provide a matrix having any number of desired unit cells. For example, a matrix can include 9216 unit cells arranged in 96 rows and 96 columns. Hence, embodiments of the present invention provide a high density format for reacting a plurality of samples with a plurality of reagents, for example, ninety-six (96) samples with ninety-six (96) reagents.

Microfluidic device features such as channels, valves, chambers, are often at least partially contained, embedded, or formed by or within one or more layers of an elastomeric block 380. As shown here with reference to the "A1" arrows, a first material such as a reagent can flow through a first channel $330_{(1)}$, past or through a plurality of first isolation valves $332_{(1,1)}$, $332_{(1,2)}$, and into a plurality of first chambers $340_{(1,1)}$, $340_{(1,2)}$, respectively. Likewise, with reference to the "A2" arrows, a second material such as a reagent can flow through a first channel $330_{(2)}$, past or through a plurality of first isolation valves $332_{(2,1)}$, $332_{(2,2)}$, and into a plurality of first chambers $340_{(2,1)}$, $340_{(2,2)}$, respectively. In some embodiments, materials flow through first channel $330_{(1)}$ and first channel $330_{(2)}$ in the same direction. In some embodiments, material flowing through first channel $330_{(1)}$ travels in a direction opposite from material flowing through first channel $330_{(2)}$. With reference to the "B1" arrows, a third material such as a sample can flow through a second channel $310_{(1)}$, past or through a plurality of second isolation valves $312_{(1,1)}$, $312_{(2,1)}$, and into a plurality of second chambers $320_{(1,1)}$, $320_{(2,1)}$, respectively. Hence, embodiments of the present invention provide microfluidic techniques whereby a material can be flowed through a common passage or trunk of a channel, such as second channel $310_{(1)}$, and into a plurality of individual branches stemming from the common trunk, such as those branch channels which individually feed into second chambers $320_{(1,2)}$, $320_{(2,2)}$. Similarly, with reference to the "B2" arrows, a fourth material such as a sample can flow through a second channel $310_{(2)}$, past or through a plurality of second isolation valves $312_{(1,2)}$, $312_{(2,2)}$, and into a plurality of second chambers $320_{(1,2)}$, $320_{(2,2)}$, respectively. In some embodiments, materials flow through second channel $310_{(1)}$ and second channel $310_{(2)}$ in the same direction. In some embodiments, material flowing through second channel $310_{(1)}$ travels in a direction opposite from material flowing through second channel $310_{(2)}$. As shown in FIG. 3, material flowing through second channel $310_{(1)}$ and material flowing through second channel $310_{(2)}$ travel in opposing directions "B1" and "B2", respectively. Hence, when loading multiple samples into an elastomeric layered block, some samples can be introduced through routing lines on one side of the block, and some samples can be introduced through routing lines on an opposing side of the block. This allows for an even distribution or placement of sample loading route lines on opposite sides of the block, instead of placing all or most sample loading route lines on the same side of the block. Because the sum total of the sample routing lines are divided between different sides of the block, more sample routing lines can be introduced into the block. Consequently, a greater number of samples can be analyzed within the block during a single procedure.

To allow flow from the plurality of first channels $330_{(1)}$, $330_{(2)}$ into the plurality of first reaction chambers $340_{(1,1)}$, $340_{(1,2)}$, $340_{(2,1)}$, $340_{(2,2)}$, each of the plurality of first isolation valves $332_{(1,1)}$, $332_{(1,2)}$, $332_{(2,1)}$, $332_{(2,2)}$ is in an open valve state. To allow flow from the plurality of second channels $310_{(1)}$, $310_{(2)}$ into the plurality of second reaction chambers $320_{(1,1)}$, $320_{(1,2)}$, $320_{(2,1)}$, $320_{(2,2)}$, each of the plurality of second isolation valves $312_{(1,1)}$, $312_{(1,2)}$, $312_{(2,1)}$, $312_{(2,2)}$ is in an open valve state. To prevent or inhibit flow between each of the plurality of first reaction chambers $340_{(1,1)}$, $340_{(1,2)}$, $340_{(2,1)}$, $340_{(2,2)}$ and their corresponding counterpart of the plurality of second reaction chambers $320_{(1,1)}$, $320_{(1,2)}$, $320_{(2,1)}$, $320_{(2,2)}$ through their corresponding counterpart of the plurality of reaction channels $370_{(1,1)}$, $370_{(1,2)}$, $370_{(2,1)}$, $370_{(2,2)}$, respectively, each of the plurality of interface valves $362_{(1,1)}$, $362_{(1,2)}$, $362_{(2,1)}$, $362_{(2,2)}$, respectively, is in a closed valve state. Under such conditions, first channel $330_{(1)}$ is in fluid communication with first reaction chambers $340_{(1,1)}$, $340_{(1,2)}$, first channel $330_{(2)}$ is in fluid communication with first reaction chambers $340_{(2,1)}$, $340_{(2,2)}$, second channel $310_{(1)}$ is in fluid communication with second reaction chambers $320_{(1,1)}$, $320_{(2,1)}$, and second channel $310_{(2)}$ is in fluid communication with second reaction chambers $320_{(1,2)}$, $320_{(2,2)}$. Fluid communication between first chambers $340_{(1,1)}$, $340_{(1,2)}$, $340_{(2,1)}$, $340_{(2,2)}$ and second chambers $320_{(1,1)}$, $320_{(1,2)}$, $320_{(2,1)}$, $320_{(2,2)}$, respectively, is interrupted.

A first material can be loaded into first reaction chambers $340_{(1,1)}$, $340_{(1,2)}$ via first channel $330_{(1)}$. A second material can be loaded into first reaction chambers $340_{(2,1)}$, $340_{(2,2)}$ via first channel $330_{(2)}$. A third material can be loaded into second reaction chambers $320_{(1,1)}$, $320_{(2,1)}$ via second channel $310_{(1)}$. A fourth material can be loaded into second reaction chambers $320_{(1,2)}$, $320_{(2,2)}$ via second channel $310_{(2)}$. Optionally, such materials can be loaded into the chambers under a desired or selected pressure. Control channel $350_{(1)}$ can be activated so as to transform each of first isolation valves $332_{(1,1)}$, $332_{(2,1)}$ and second isolation valves $312_{(1,1)}$, $312_{(2,1)}$ from an open valve state to a closed valve state. Similarly, control channel $350_{(2)}$ can be activated so as to transform each of first isolation valves $332_{(1,2)}$, $332_{(2,2)}$ and second isolation valves $312_{(1,2)}$, $312_{(2,2)}$ from an open valve state to a closed valve state. In this way the materials can be confined or maintained, optionally under pressure, within the reaction chambers.

FIG. 4 illustrates another perspective view of matrix 300 having four unit cells $300_{(1,1)}$, $300_{(1,2)}$, $300_{(2,1)}$, $300_{(2,2)}$. As shown here with reference to the "A" arrows, the first material can flow from first reaction chamber $340_{(1,1)}$, through reaction channel $370_{(1,1)}$, past interface valve $362_{(1,1)}$, and into second reaction chamber $320_{(1,1)}$, where the first material can contact the third material. To allow such flow through reaction channel $370_{(1,1)}$, the interface channel $360_{(1)}$ can be activated so as to transform interface valve $362_{(1,1)}$ from a closed valve state to an open valve state. Under such conditions, first reaction chamber $340_{(1,1)}$ and second reaction chamber $320_{(1,1)}$ are in fluid communication via reaction channel $370_{(1,1)}$. Often, the presence, absence, or extent of any reaction between the first and third materials within second reaction chamber $320_{(1,1)}$ can be confirmed, detected, or quantified by inspection, for example with a reader or sensor 390.

With reference to the "B" arrows, the first material can flow from first reaction chamber $340_{(1,2)}$, through reaction channel $370_{(1,2)}$, past interface valve $362_{(1,2)}$, and into second reaction chamber $320_{(1,2)}$, where the first material can contact the fourth material. To allow such flow through reaction channel $370_{(1,2)}$, the interface channel $360_{(1)}$ can be activated so as to transform interface valve $362_{(1,2)}$ from a closed valve state to an open valve state. Under such conditions, first reaction chamber $340_{(1,2)}$ and second reaction chamber $320_{(1,2)}$ are in fluid communication via reaction channel $370_{(1,2)}$. Often, the presence, absence, or extent of any reaction between the first and third materials within second reaction chamber $340_{(1,2)}$ can be confirmed, detected, or quantified by inspection, for example with a reader or sensor 390.

With reference to the "C" arrows, the second material can flow from first reaction chamber $340_{(2,1)}$, through reaction channel $370_{(2,1)}$, past interface valve $362_{(2,1)}$, and into second reaction chamber $320_{(2,1)}$, where the second material can contact the third material. To allow such flow through reaction channel $370_{(2,1)}$, the interface channel $360_{(2)}$ can be activated so as to transform interface valve $362_{(2,1)}$ from a closed valve state to an open valve state. Under such conditions, first reaction chamber $340_{(2,1)}$ and second reaction chamber $320_{(2,1)}$ are in fluid communication via reaction channel $370_{(2,1)}$. Often, the presence, absence, or extent of any reaction between the first and third materials within second reaction chamber $320_{(2,1)}$ can be confirmed, detected, or quantified by inspection, for example with a reader or sensor 390.

With reference to the "D" arrows, the second material can flow from first reaction chamber $340_{(2,2)}$, through reaction channel $370_{(2,2)}$, past interface valve $362_{(2,2)}$, and into second reaction chamber $320_{(2,2)}$, where the second material can contact the fourth material. To allow such flow through reaction channel $370_{(2,2)}$, the interface channel $360_{(2)}$ can be activated so as to transform interface valve $362_{(2,2)}$ from a closed valve state to an open valve state. Under such conditions, first reaction chamber $340_{(2,2)}$ and second reaction chamber $320_{(2,2)}$ are in fluid communication via reaction channel $370_{(2,2)}$. Often, the presence, absence, or extent of any reaction between the fourth and second materials within second reaction chamber $320_{(2,2)}$ can be confirmed, detected, or quantified by inspection, for example with a reader or sensor 390.

Figure 5A:
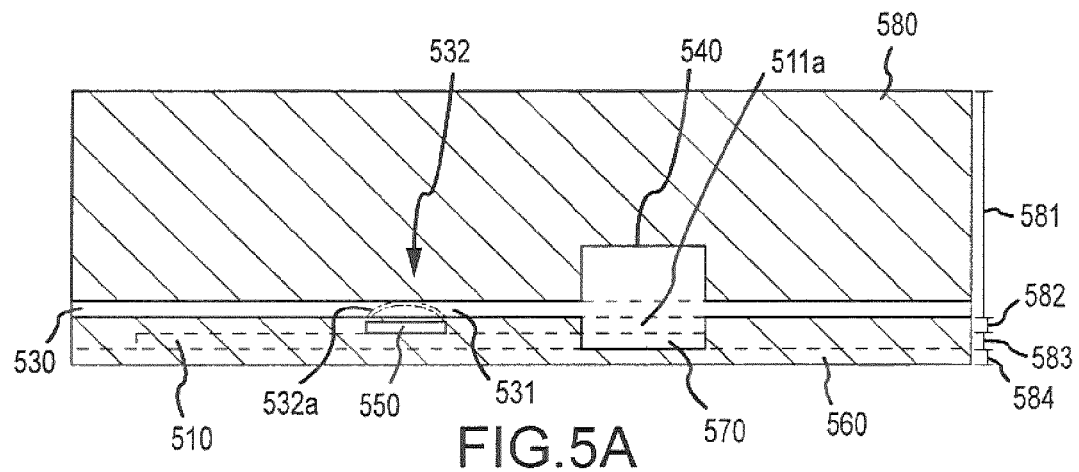
FIGS. 5A to 5C show cross-section views of a microfluidic device unit cell according to embodiments of the present invention.
Figure 5B:
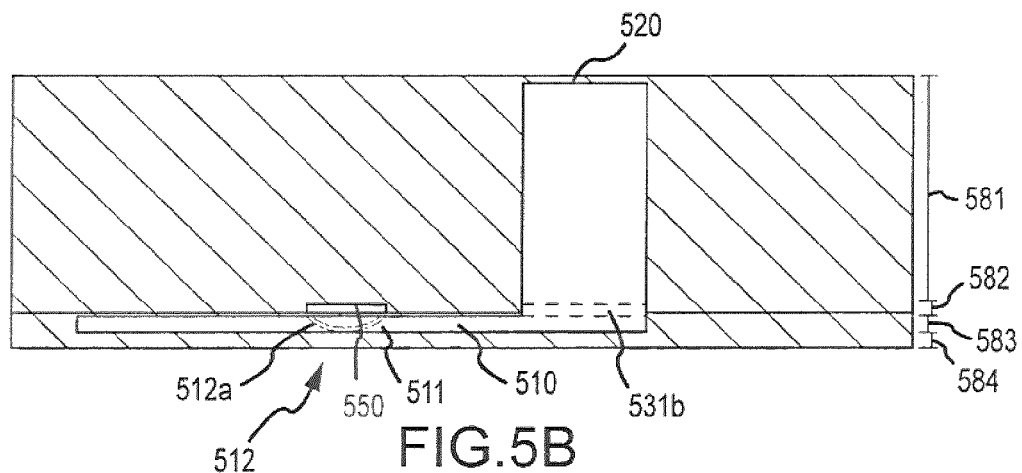
Figure 5C:
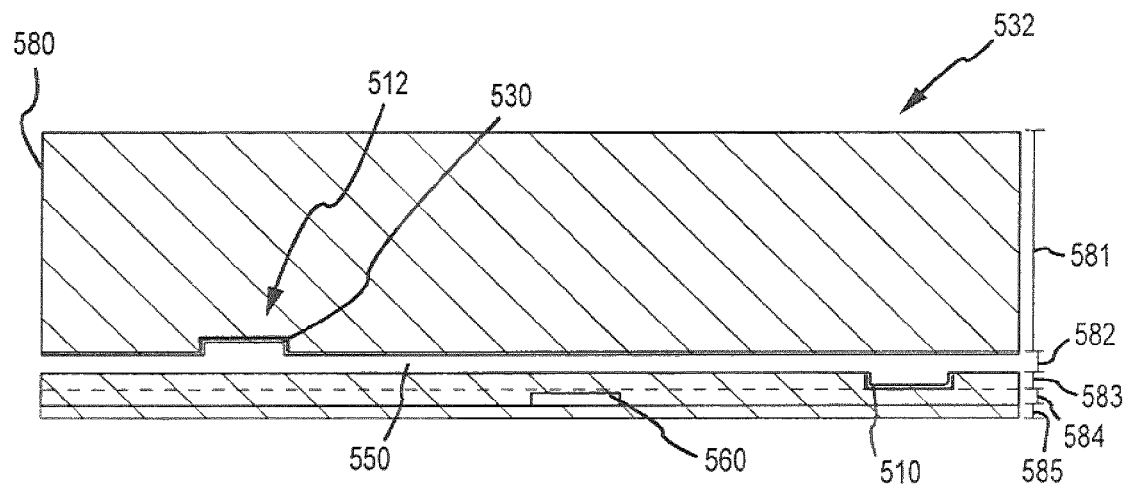

In some embodiments, the terms isolation valve and containment valve may be used interchangeably. Similarly, the terms interface valve and reaction valve may be used interchangeably. Such valves can be actuated or activated or otherwise controlled by any of a variety of valve operation methods or configurations. Exemplary valve systems and techniques which are well suited for use with embodiments of the present invention are described, for example, in U.S. Pat. No. 6,408,878, the content of which is incorporated herein by reference. Often, such valves include an elastomeric portion that, when actuated, deflects into a recess. For example, FIG. 5A shows a side view or cross section of a microfluidic device unit cell 500. The unit cell includes a first channel 530 and first sample chamber 540 in a first layer 581 of an elastomeric block 580, control channel 550 and via 511a in a second layer 582, and a reaction channel 570 in a third layer 583. An isolation valve 532 can be actuated, so as to inhibit or prevent flow through first channel 530. Actuation of isolation valve 532 can involve the deflection of an elastomeric portion 532a into a recess 531 of first channel 530. Fourth layer 584 includes interface channel 560. FIG. 5B shows another side view or cross section of microfluidic device unit cell 500. The unit cell includes a sample chamber 520 in a first layer 581, a control channel 550 and via 531b in a second layer 582, and a second channel 510 in a third layer 583. Isolation valve 512 can be actuated, so as to inhibit or prevent flow through second channel 510. Actuation of isolation valve 512 can involve the deflection of an elastomeric portion 512a into a recess 511 of second channel 510. FIG. 5C shows a side view or cross section which is orthogonal to the side views of FIGS. 5A and 5B. As depicted here, actuation of control channel 550 can operate to activate both isolation valve 532 and isolation valve 512. For example, by changing the pressure of fluid within control channel or containment line 550, it is possible to simultaneously deflect a first elastomeric portion upward into first channel 530 and a second elastomeric portion downward into second channel 510. Optionally this can result in the containment or isolation of a first material within a first chamber and a second material within a second chamber. As shown in FIG. 5C, first channel 530 and second channel 510 each present a rectangular cross section. In some instances, either or both of these channels can present a dome shaped cross section, where the dome is upright with regard to first channel 530 and inverted with regard to second channel 510.

Figure 6A:
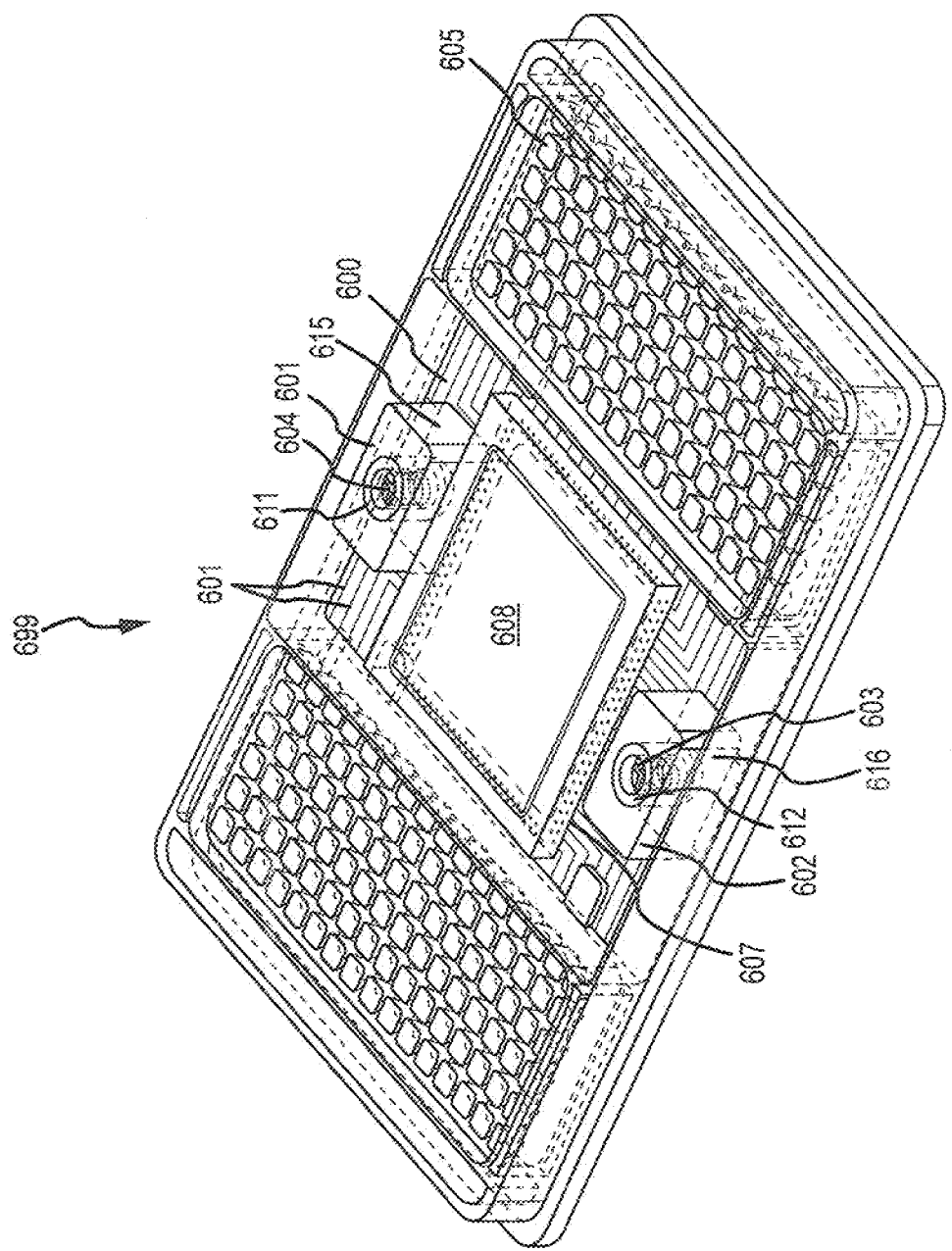
FIGS. 6A and 6B show a microfluidic device according to embodiments of the present invention.
Figure 6B:
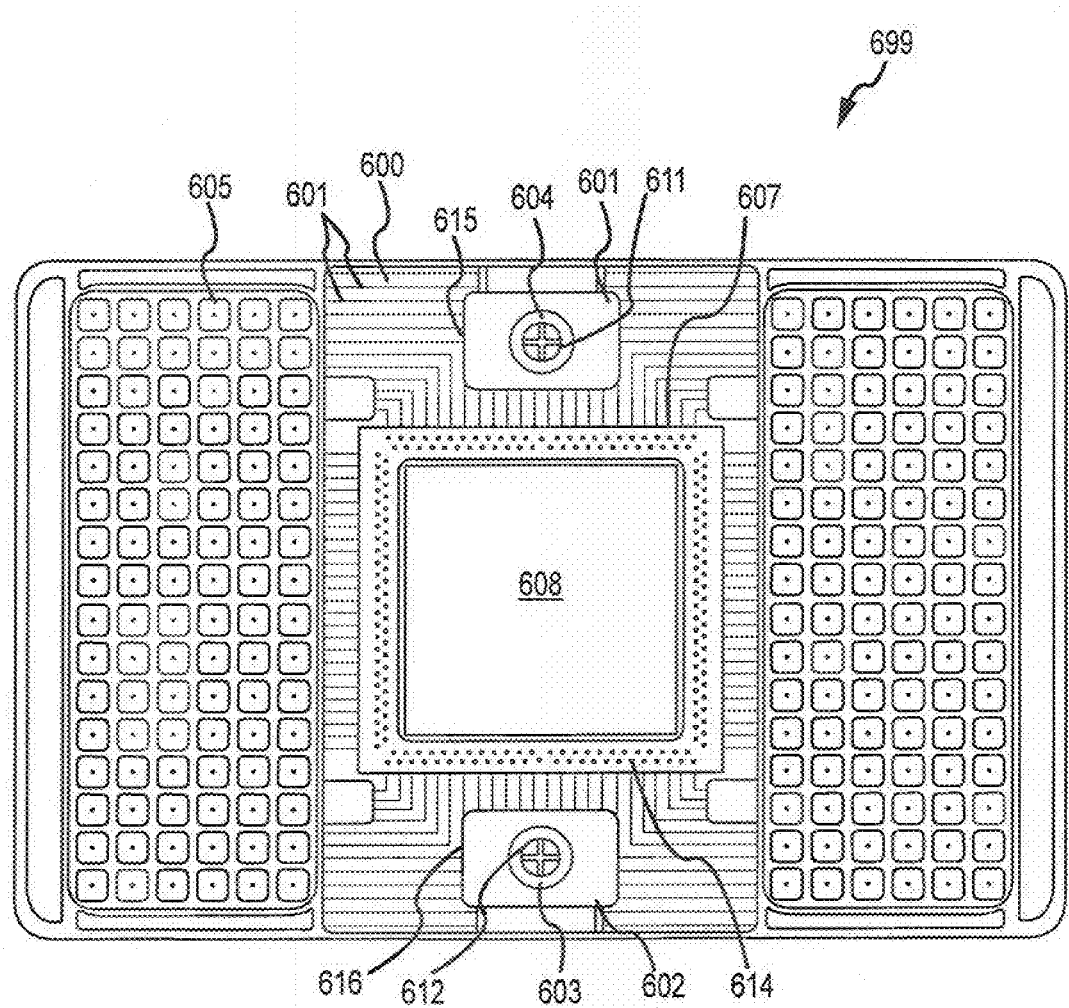

FIG. 6A illustrates a microfluidic device 699 according to embodiments of the present invention. Materials can be delivered from wells 605 toward elastomeric block 608 through passages or routing lines 601. FIG. 6B depicts microfluidic device 699 in a plan view. Microfluidic device 699 includes a substrate 600 with integrated pressure accumulator wells 601 and 602, each having a receptacle 603, 604 that contains a valve, such as a check valve. Microfluidic device 699 also includes one or more wells 605 for receiving materials such as samples or reagents, and one or more channels or routing lines disposed between wells 605 and an elastomeric block location 607 of substrate 600. An elastomeric block 608 can be coupled with substrate 600 at elastomeric block location 607. Elastomeric block can include one or more layers of elastomeric material having microfabricated recesses or channels formed therein. Elastomeric block 608 can be coupled with substrate 600 in any of a variety of ways. For example, the elastomeric block can be attached or bonded with the substrate. In some cases, the block is directly bonded to the substrate. In some cases, the block is coupled with the substrate without the use of an adhesive. In some cases, the block is coupled with the substrate with an adhesive. Within elastomeric block 608 are one or more channels in fluid communication with one or more vias 614, which in turn provide fluid communication between the elastomeric block channels and the substrate channels. Hence, the substrate channels can provide fluid communication between wells 605 and channels within the elastomeric block.

Accumulator wells 601, 602 often include valves 611, 612, respectively, which can be check valves for introducing and holding gas of fluid under pressure into accumulator chambers 615 and 616. Valves 611 and 612 are situated inside of receptacles 604 and 603, respectively, which can keep liquid, when present in accumulator chambers 615 and 616, from contacting valves 611 and 612. In some embodiments, valves 611 and 612 may be mechanically opened by pressing a shave, pin or the like, within a check valve to overcome a self closing force of the check valve, thereby permitting release of pressure from the accumulator chamber, or reducing fluid pressure contained within the accumulator chamber.

Substrate 600 and associated components may be fabricated from polymers, such as polypropylene, polyethylene, polycarbonate, high-density polyethylene, polytetrafluoroethylene PTFE or Teflon®, glass, quartz, transparent materials, polysilicon, metals, such as aluminum, or the like. Any of a variety of gases, liquids, or fluids can be introduced into accumulator chambers 615 and 616. In some cases, valves 611 and 612 can be actuated to release fluid pressure otherwise held inside of accumulator chambers 615 and 616. Optionally, a portion of substrate 600 beneath the elastomeric block region 607 can be transparent. In some cases, the portion may be opaque or reflective. Accumulator chambers 601 and 602 can be in fluid communication with channels contained in elastomeric block region 607, and ultimately, with channels contained in elastomeric block 608. Accumulator operation is described in U.S. Patent Publication No. 2007/0196912, the content of which is incorporated herein by reference. In some cases, operation of a channel, such as a control channel 150 as shown in FIG. 1, can be modulated or controlled by an accumulator.

Figure 7:
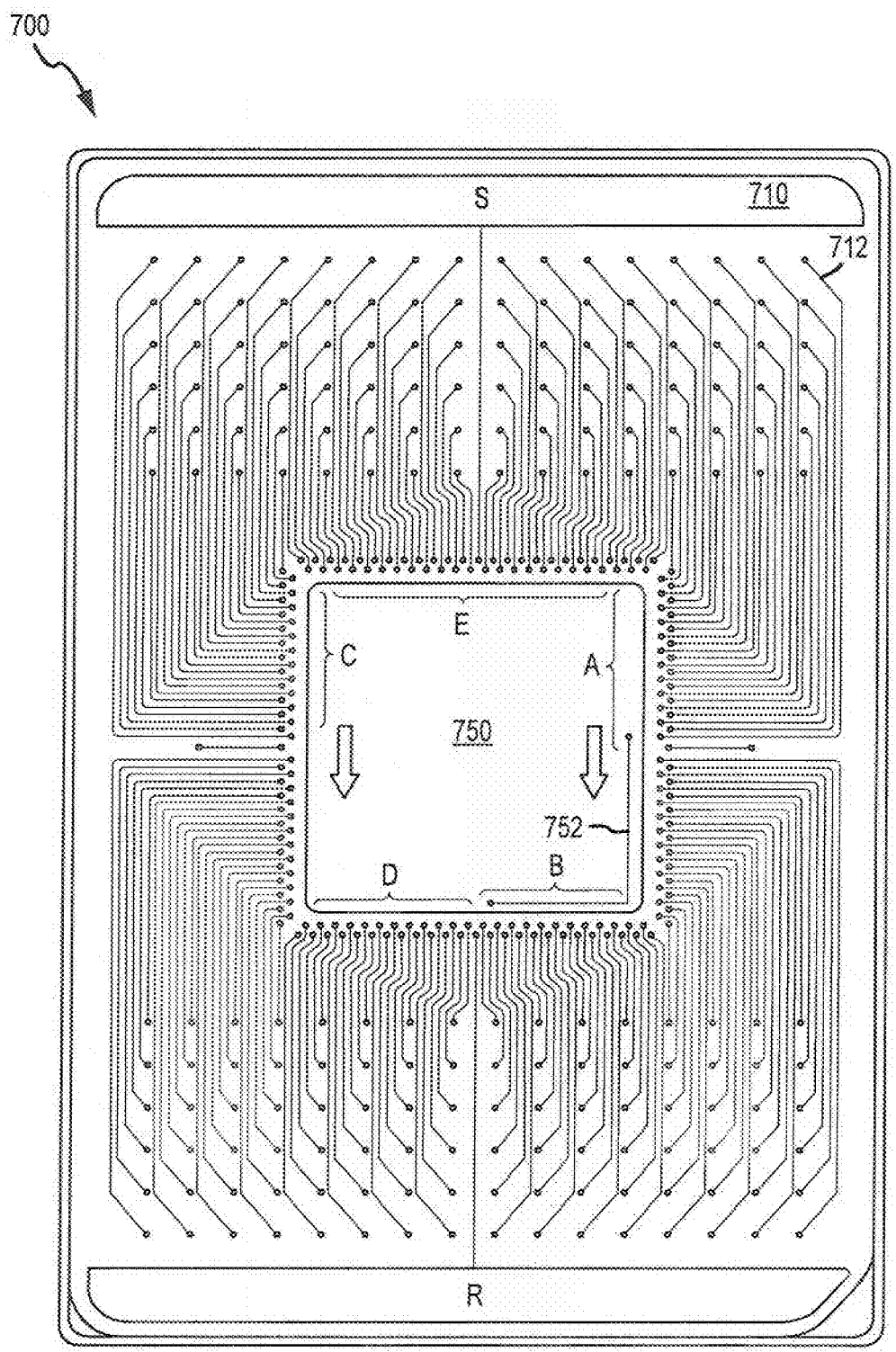
FIG. 7 illustrates a microfluidic device according to embodiments of the present invention.

FIG. 7 illustrates a microfluidic device 700 according to embodiments of the present invention. Device 700 includes a carrier 710 coupled with a chip or block 750. Carrier or frame 710 includes a plurality of routing lines 712 configured to allow flow from carrier wells toward chip 750. For example, routing lines disposed on the "S" side of the carrier can provide for the passage of sample, and routing lines disposed on the "R" side of the carrier can provide for the passage of reagent. In some cases, chip 750 can also include a plurality of routing lines 752. For example, routing lines on the chip can provide material transport on the chip from location A to location B, and from location C to location D. In this way, a portion of the samples loaded onto the carrier can be transported to location E of the chip, and another portion of the samples loaded onto the carrier can be transported to locations D and B of the chip, such that some sample is loaded at one side of the block, and some sample is loaded at an opposing side of the block, as further discussed herein with reference to FIG. 3.

Figure 8:
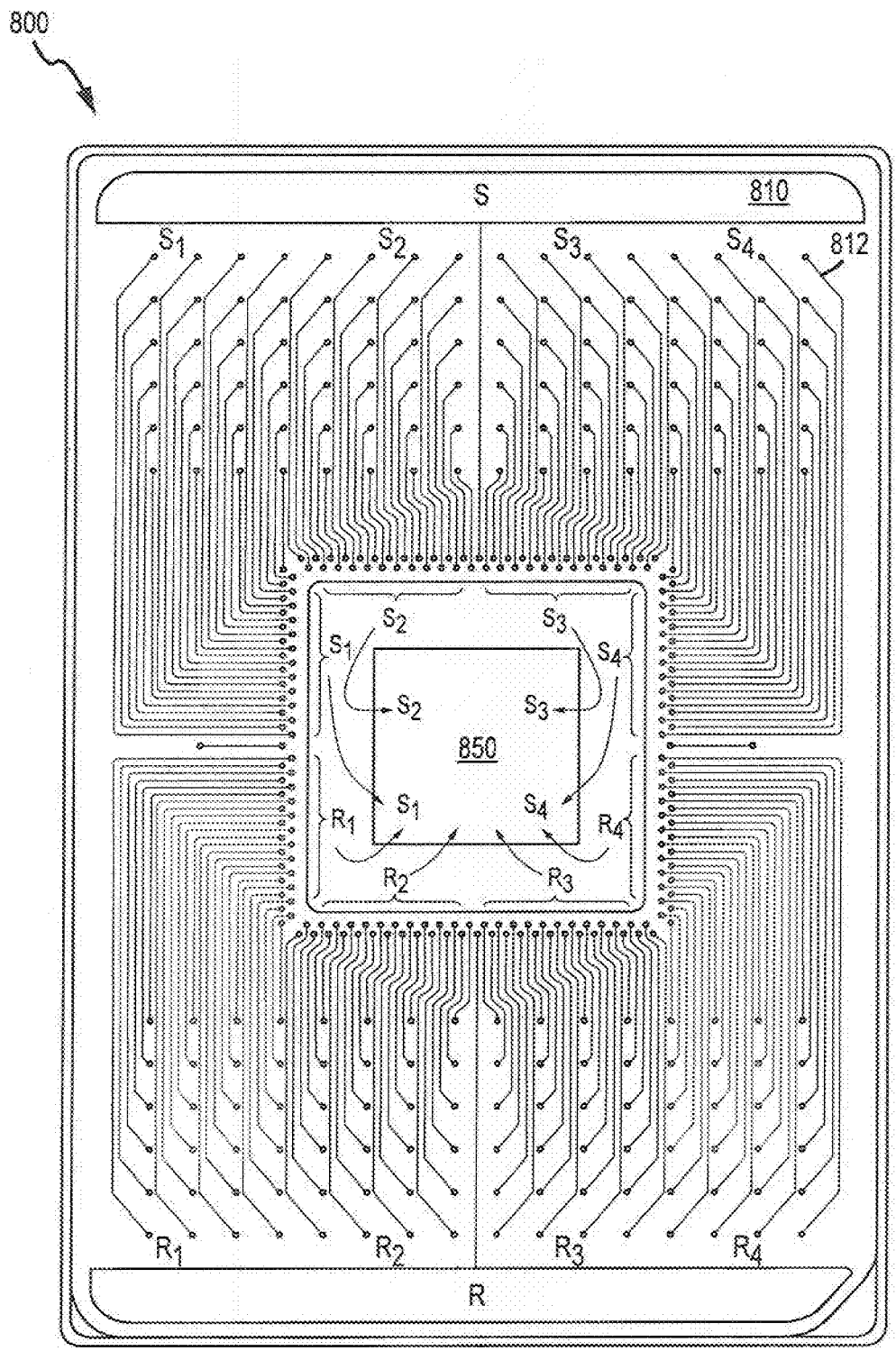
FIG. 8 illustrates a microfluidic device according to embodiments of the present invention.

FIG. 8 illustrates a microfluidic device 800 according to embodiments of the present invention. Device 800 includes a carrier 810 coupled with a chip or block 850. Carrier or frame 810 includes a plurality of routing lines 812 configured to allow flow from carrier wells toward chip 850. For example, routing lines disposed on the "S" side of the carrier can provide for the passage of sample, and routing lines disposed on the "R" side of the carrier can provide for the passage of reagent. As shown in this illustration, 24 samples loaded into wells at zone $S_1$ flow to the left side of the chip (upper half), 24 samples loaded into wells at zone $S_2$ flow to the upper side of the chip (left half), 24 samples loaded into wells at zone $S_3$ flow to the upper side of the chip (right half), and 24 samples loaded into wells at zone $S_4$ flow to the right side of the chip (upper half). Thereafter, through another set of routing lines optionally disposed at or within the elastomeric block, the $S_1$ samples flow to the left side of the chip (lower half), the $S_2$ samples flow to the left side of the chip (upper half), the $S_3$ samples flow to the right side of the chip (upper half), and the $S_4$ samples flow to the right side of the chip (lower half). Further, 24 reagent portions loaded into wells at zone $R_1$ flow to the left side of the chip (lower half), 24 reagent portions loaded into wells at zone $R_2$ flow to the lower side of the chip (left half), 24 reagent portions loaded into wells at zone $R_3$ flow to the lower side of the chip (right half), and 24 reagent portions loaded into wells at zone $R_4$ flow to the right side of the chip (lower half). Thereafter, through another set of routing lines optionally disposed at or within the elastomeric block, the $R_1$ reagent portions flow to the lower side of the chip (left half), the $R_2$ reagent portions flow to the lower side of the chip (left half), the $R_3$ reagent portions flow to the lower side of the chip (right half), and the $R_4$ samples flow to the lower side of the chip (right half). Hence, routing lines on or in the chip can provide material transport on or through the chip from one location to another. In this way, a portion of the samples loaded at one end of the carrier (e.g. the "S" end) can be transported such that some sample is loaded at one side of the block, and some sample is loaded at an opposing side of the block, as further discussed herein with reference to FIG. 3.

In some embodiments, microfluidic devices may contain blind flow channels which include a region that functions as a reaction chamber or reaction site. Blind flow, or blind fill, can refer to the filling of a dead-end tube or lumen with a liquid where a head of gas is pushed in front of the liquid bolus, and where that head of gas is vented or otherwise released from the lumen, allowing the dead-end lumen to fill fully with the liquid. In some embodiments, polydimethylsiloxane (PDMS) can be used as an elastomeric material. PDMS is sufficiently gas permeable that liquid pressurized at a few psi can drive the gas out of the channels, leaving them completely filled with liquid.

Table 1 provides an exemplary experimental design where various materials can be loaded or introduced into a microfluidic device that includes four unit cells. According to this table, sample can be flowed through first channels and reagent can be flowed through second channels. It is understood that alternatively, reagent can be flowed through first channels and sample can be flowed through second channels. Embodiments of the present invention encompass techniques were sample is flowed through a set of first channels and a set of second channels, and reagent is flowed through a set of first channels and a set of second channels.

TABLE 1

| channel | material | chamber |
| --- | --- | --- |
| first channel $330_{(1)}$ | DNA sample from person A | first chambers $340_{(1,\,1)}$, $340_{(1,\,2)}$ |
| first channel $330_{(2)}$ | DNA sample from person B | first chambers $340_{(2,\,1)}$, $340_{(2,\,2)}$ |
| second channel $310_{(1)}$ | disease X gene primers/probes | second chambers $320_{(1,\,1)}$, $320_{(2,\,1)}$ |
| second channel $310_{(2)}$ | disease Y gene primers/probes | second chambers $320_{(1,\,2)}$, $320_{(2,\,2)}$ |

Table 2 shows the mixtures occurring in the microfluidic device reaction chambers, and the experimental inquiries which can be answered, for example, by conducting a PCR reaction where the sample contains patient DNA and the reagent contains an oligonucleotide primer and probe set.

TABLE 2

| reaction chamber | materials mixed | inquiry |
| --- | --- | --- |
| second chamber $320_{(1,\,1)}$ | DNA sample from person A disease X gene primer/probe | person A has gene for disease X? |
| second chamber $320_{(1,\,2)}$ | DNA sample from person A disease Y gene primer/probe | person A has gene for disease Y? |
| second chamber $320_{(2,\,1)}$ | DNA sample from person B disease X gene primer/probe | person B has gene for disease X? |
| second chamber $320_{(2,\,2)}$ | DNA sample from person B disease Y gene primer/probe | person B has gene for disease Y? |

It is understood that any of a variety of materials may be mixed or reacted in according to embodiments of the present invention. For example, genotyping applications may involve detecting the presence or absence of a target in a sample. Gene expression applications may involve measuring or quantifying amounts of materials contained in a sample. Such applications may benefit from the enhanced mixing function provided by embodiments of the present invention. Further, microfluidic devices and methods can be used to crystallize a protein. In one embodiment a method includes providing a microfluidic device having a first chamber having a dimension between 1000 μm and 1 μm, a second chamber having a dimension between 1000 μm and 1 μm, and one or more flow or control channels each having a dimension between 1000 μm and 1 μm. The first and second chambers can be in fluid communication with each other through a channel. A valve can be disposed along a channel which, when actuated to open or close, controls fluid communication between the first and second chambers, or into or out of the first or second chamber, or both. The method can include introducing a crystallization reagent into the first chamber, introducing the protein in a solution into the second chamber, opening a valve so that the solution containing the protein in the second chamber becomes in fluid communication with the crystallization reagent in the first chamber, and closing the valve after a period of time to interrupt fluid communication between the first and second chambers.

In some embodiments, a valve can be under the control of an automated valve actuating device, which in turn may be further under control of a computer or processor. A multilayer microfluidic device can include at least one elastomeric layer, and a valve can include a deflectable membrane. In some cases, a deflectable membrane of a valve can be deflectable into one or more channels to control fluid movement along the channels. Multiple elastomeric membranes may be bonded or adhered together to form an elastomeric block. In some cases, portions of channels or chambers can overlap with portions of other channels or chambers at an overlap region. Such channels or chambers can be in fluid communication through a via located at the overlap region.

Figure 9:
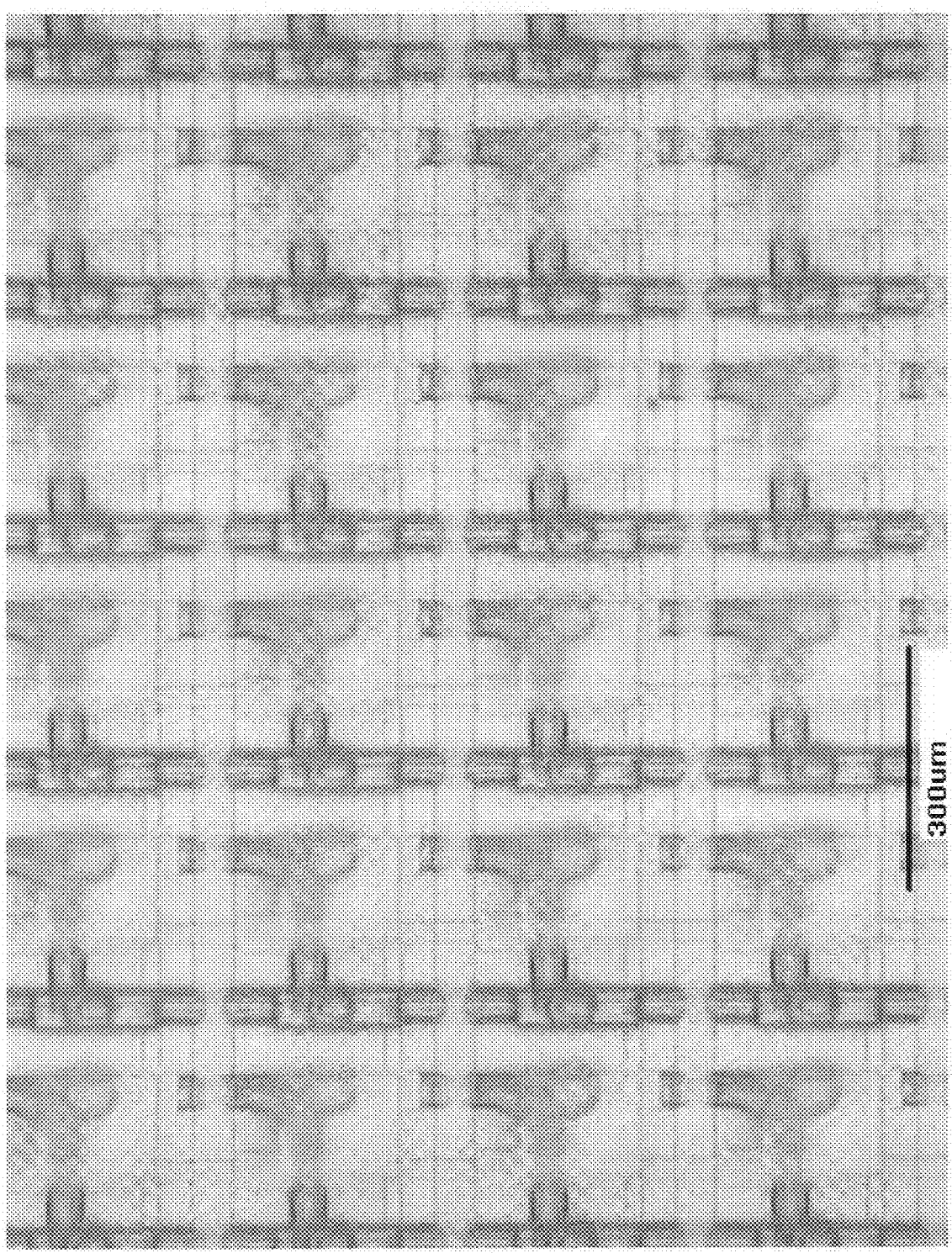
FIG. 9 illustrates a photomicrograph, with scale bar, of an exemplary microfluidic device according to embodiments of the present invention.
Figure 10:
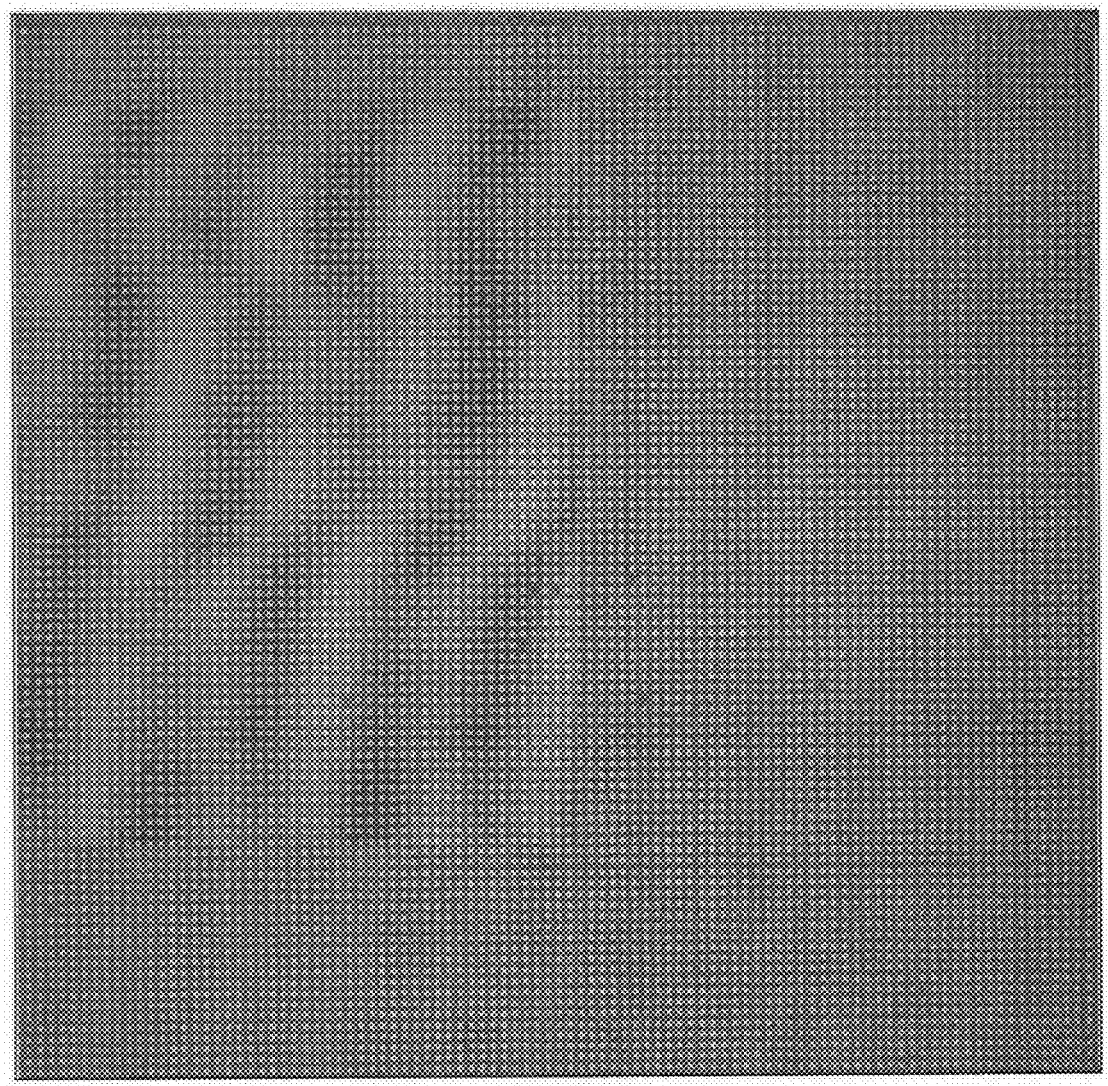
FIG. 10 illustrates a reader image of an exemplary microfluidic device according to embodiments of the present invention.
Figure 11:
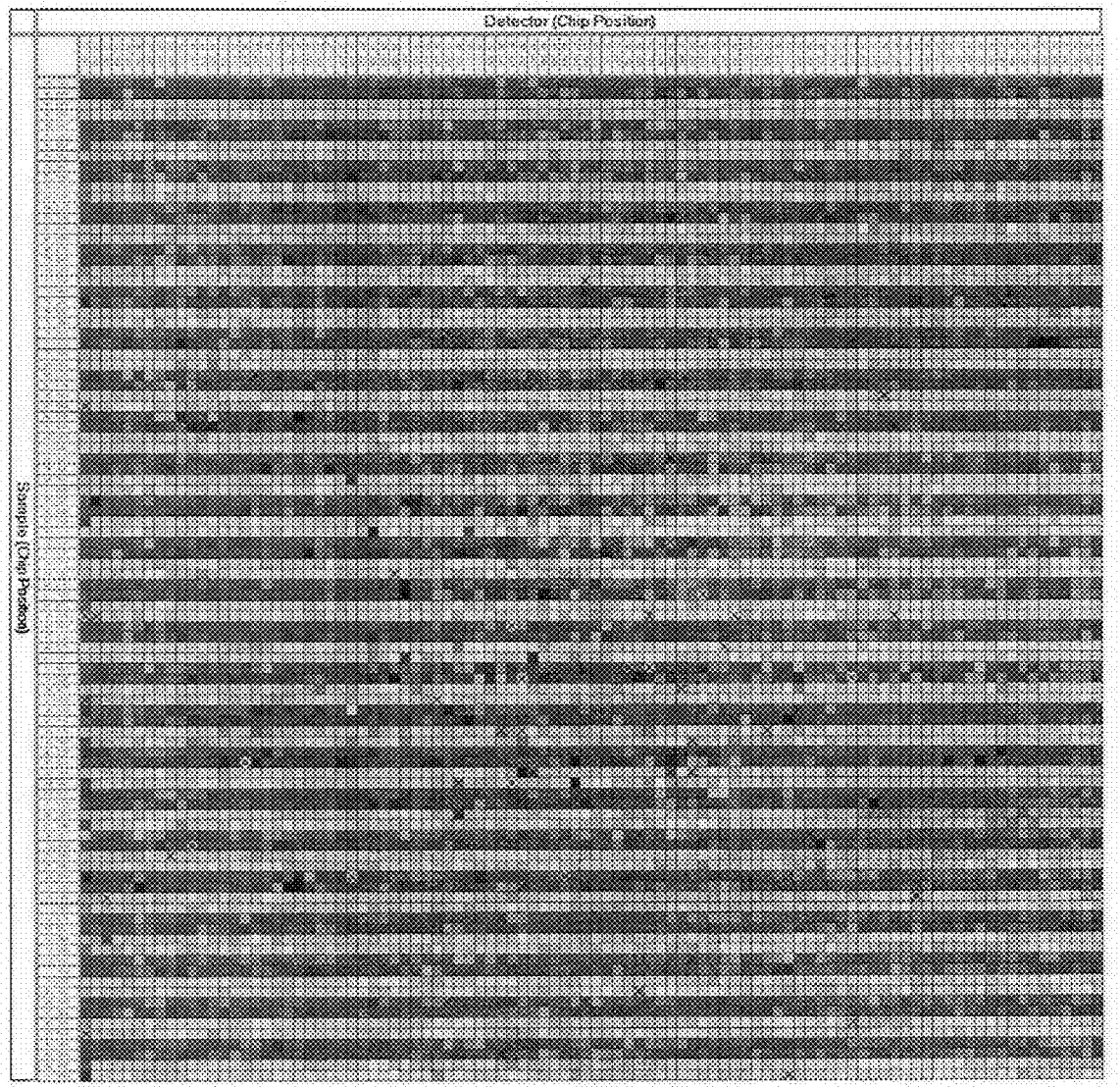
FIG. 11 illustrates a reader image of an exemplary microfluidic device according to embodiments of the present invention.
Figure 12:
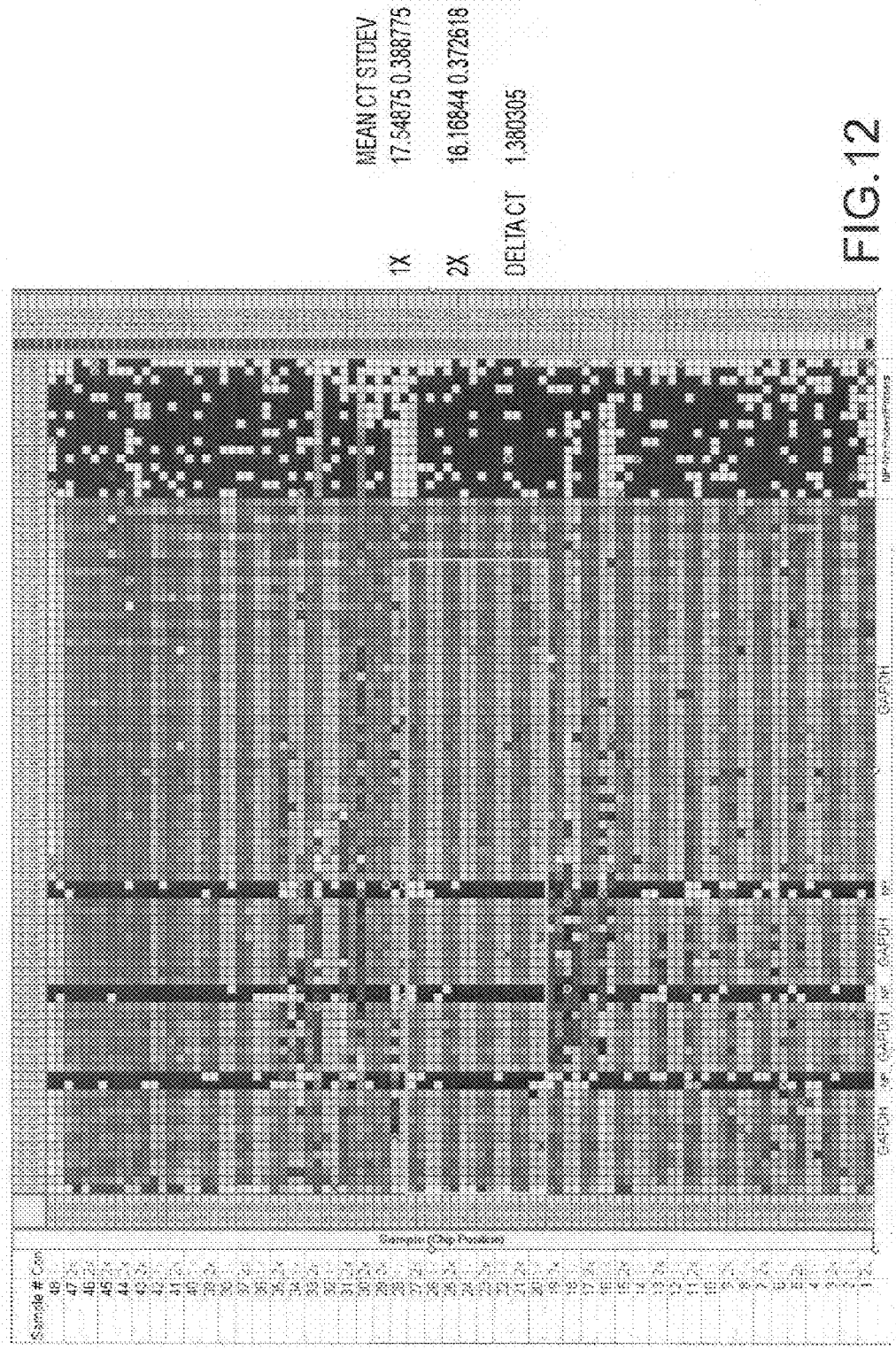
FIG. 12 illustrates a reader image of an exemplary microfluidic device according to embodiments of the present invention.
Figure 13:
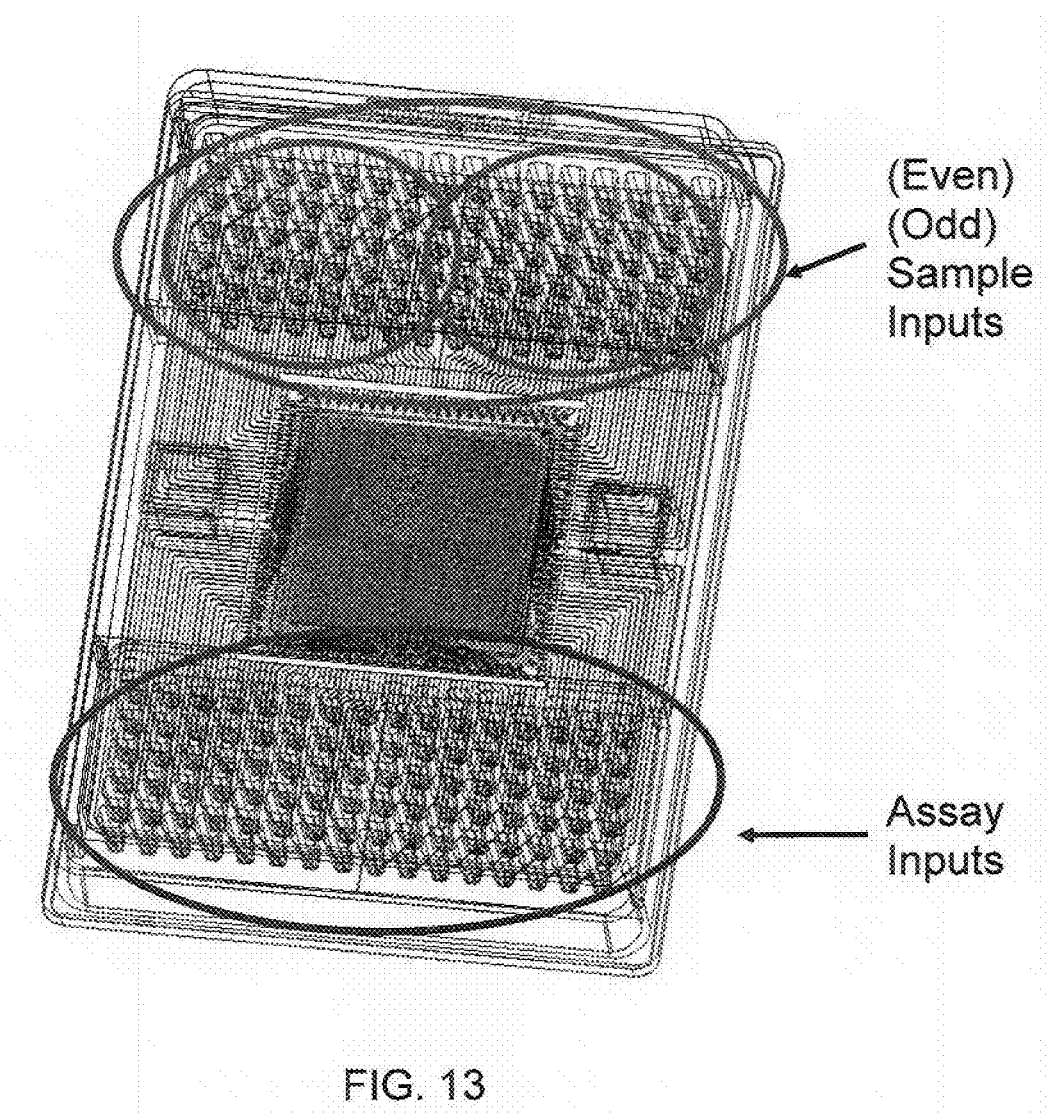
FIG. 13 illustrates an exemplary microfluidic device, showing channel connections between input wells and an elastomeric block, according to embodiments of the present invention.
Figure 14:
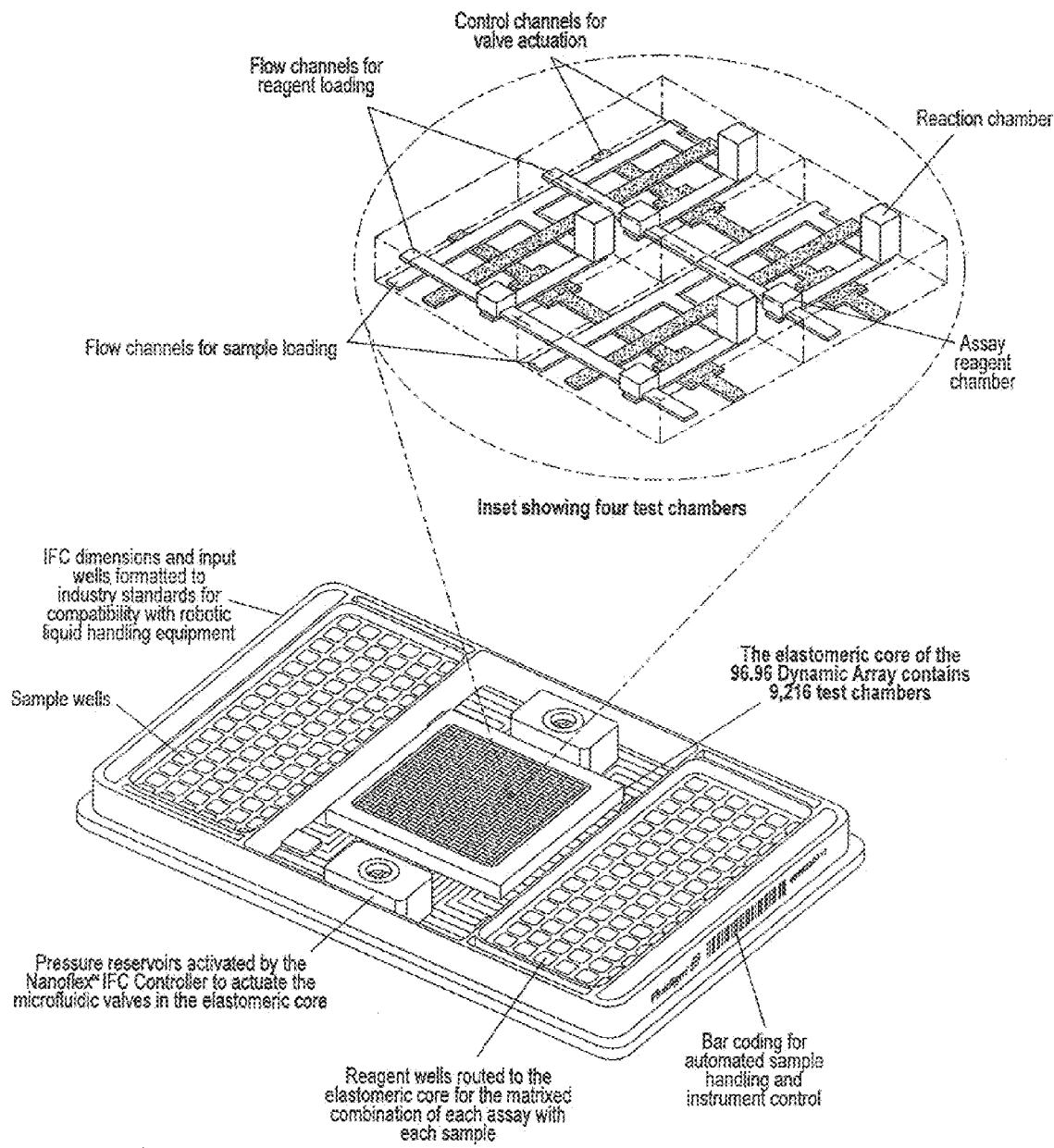
FIG. 14 illustrates aspects of a microfluidic system and method according to embodiments of the present invention.

FIGS. 9-13 disclose additional aspects of microfluidic systems and methods according to embodiments of the present invention. FIG. 9 shows a photomicrograph, with scale bar, of an exemplary microfluidic device. FIGS. 10-12 each show reader images of exemplary microfluidic devices and experimental results provided by the devices. FIG. 13 illustrates an exemplary microfluidic device, showing channel connections between input wells and an elastomeric block. As shown in FIG. 13, a microfluidic system can include a microfluidic device having a multiwell plate, optionally referred to as a carrier or frame. Often, the multiwell plate includes a plastic material, such as an injection molded plastic. The multiwell plate can include channel connections or passages for providing fluid communication between input wells and an elastomeric block. U.S. Patent Application No. 61/030,887 filed Feb. 22, 2008, (Integrated Carrier for Microfluidic Device) which is incorporated herein by reference, describes carrier or frame configurations which are suitable for use with microfluidic systems and methods of the instant application. FIG. 14 shows further aspects of microfluidic systems and methods according to embodiments of the present invention.

Additional embodiments of the invention include methods for detecting nucleic acid analytes through their interactions with a nucleic acid probe, such as a hydrolysis probe, a hairpin probe, a padlock probe (PLP) or a hybridization probe. The methods of the invention combine the features of using the high throughput microfluidic device as described herein, labeled nucleic acid probes, and homogenous assays to detect and/or quantify nucleic acid analytes with high PCR and probe specificity. Certain methods described herein may allow for the detection of low copy number nucleic acid analyte per cell, have low fluorescence background yielding a high signal to noise ratio. The homogeneous assays of the invention may have a dynamic range of at least about 3 orders of magnitude, more often at least about 4, even more often at least about 5, even more often at least about 6, often at least about 7, and sometimes at least about 8 orders of magnitude.

According to an embodiment of the invention, the detection and/or quantification of a plurality of nucleic acid analytes from a sample may generally be carried out by obtaining a pre-amplified sample, aliquoting the sample and distributing the pre-amplified sample into reaction chambers of a microfluidic device containing the appropriate buffers, primers, probes and enzymes, performing a homogenous assay for the target nucleic analytes of interest, and querying the aliquots for the presence of nucleic acid analytes.

In a first embodiment, a sample is obtained which is suspected of containing the target nucleic acid analyte of interest. The sample may be first reversed transcribed into cDNA and subjected to a preliminary amplification reaction to generate a pre-amplified sample. In the preliminary amplification reaction, the reverse transcribed sample is subjected to 14 cycles of PCR in order to increase the nucleic acid analytes by about 16,000 fold.

In a second embodiment, aliquots of the pre-amplified sample are distributed into separated compartments of a microfluidic device and combined with the appropriate reagents. In particular, the aliquot may have a volume of in the range of about 1 picoliter to about 500 nanoliters, more often in the range of about 100 picoliters to about 20 nanoliters, even more often in the range of about 1 nanoliter to about 20 nanoliters, and most often in the range of about 5 nanoliters to about 15 nanoliters. The reagents may include a labeled nucleic acid probe, PCR primers (e.g., forward primers and reverse primers), a thermostable DNA polymerase, GT buffer, an aqueous buffer, magnesium chloride and deoxynucleotide truphosphates, and may also include other non-reactive ingredients. In a specific aspect, a pre-sample mix may be prepared which may include TaqMan Universal PCR master Mix, AmpliTaq-Gold (about 5 units/μl), 20×GT buffer, and H$_2$O. The pre-sample mix may be combined with the nucleic acid of interest, and appropriate primers.

In one aspect of the invention, a 1×GT buffer may contain betaine in a range of about 0.1 M to about 0.8 M, BSA in a range of about 1 mg/ml to about 4 mg/ml, glycerol in a range of about 1% to about 5%, PEG 20,000 in a range of about 1% to about 5%, PEG MME550 in a range of about 0.05% to about 5%, MME5000 in a range of 1% about to about 5%, Superblock® in PBS in a range of about 1% to about 15%, Superblock® T20 in a range of about 1% to about 10%, and Tween 20 in a range of 0.1% about to about 3%. In a specific aspect, the 1×GT buffer may contain about 0.4 M betaine, 2 mg/ml BSA, about 2.5% glycerol, about 2% PEG 20,000, about 1% PEG MME550, about 2.5% MME5000, about 10% Superblock® in PBS, about 5% Superblock® T20, and about 0.5% Tween 20. In a more specific embodiment, the 1×GT buffer may contain about 0.4 M betaine, 4 mg/ml BSA, about 5% glycerol, about 2% PEG 20,000, about 1% PEG MME550, about 2.5% MME5000, about 10% Superblock® in PBS, about 10% Superblock® T20, and about 1% Tween 20.

In another aspect of the invention, a 20×GT buffer may be prepared and may be diluted to a final concentration of 1× when used in the dynamic arrays. For example, a 20×GT buffer may include betaine in a range of about 1M to about 10M, BSA in a range of about 5 mg/ml to about 15 mg/ml, and Superblock® T20 (in TBS) in a range of about 20% to about 65%. In a particular aspect, the GT buffer may include about 5 M betaine, about 10 mg/ml BSA, and about 57% Superblock® T20 in TBS. As one skilled in the art appreciates, the 20×GT buffer would be diluted to 1× in the final reaction mix.

The PCR primers must be sufficiently long to prime the synthesis of extension products in the presence of the agent for polymerization. The exact length and composition of the primer will depend on many factors, including temperature of the annealing reaction, source and composition of the primer, proximity of the probe annealing site to the primer annealing site, and ratio of primer:probe concentration. For example, depending on the complexity of the target sequence, the oligonucleotide primer typically contains in the range of about 15 to about 30 nucleotides, although it may contain more or fewer nucleotides. The primers should be sufficiently complementary to selectively anneal to their respective strands and form stable duplexes. One skilled in the art appreciates how to select appropriate PCR primer pairs to amplify the target nucleic acid analyte of interest.

In a third embodiment, a homogenous assay may be performed such as real-time PCR, for example. In this assay, the labeled nucleic acid probe contains a stretch of nucleic acid sequences that are capable of recognizing 8-mer and 9-mer motifs in the target nucleic acid analyte, as described above. FRET quenching of the labeled nucleic acid probe is irrevocably eliminated when the Taq polymerase reaches the region where the labeled probe is annealed to the target nucleic acid analyte, recognizes the probe-template hybrid as a substrate, and subsequently hydrolyzes phosphodiester bonds of the probe during primer-directed DNA amplification. The hydrolysis reaction irrevocably releases the quenching effect of the quencher dye on the reporter dye, thus resulting in increasing detector fluorescence with each successive PCR cycle. It will be appreciated that the invention is not limited to the use of real-time PCR, and that other variations of PCR, described above, may be used to detect and/or quantify the analyte of interest.

The homogenous assay of the invention should not be construed to be limited to PCR-based detection methods, but may employ any method of detection and/or quantification to detect and/or quantify a target nucleic acid analyte. In one aspect, PCR may be used to amplify a target. In another aspect, other amplification systems or detection systems may be used, including systems described in U.S. Pat. No. 7,118,910, which is incorporated herein by reference in its entirety. In a further aspect, a detection system other than PCR may be used such as an Invader® assay (Third Wave, Madison, Wis.). In one aspect, real time quantification methods may be used to determine the quantity of a target nucleic acid analyte present in a sample by measuring the amount of amplification product formed during or after the amplification process itself. Fluorogenic nuclease assays are one specific example of a real time quantification method that may be used successfully with the matrix-type microfluidic devices described herein. This method of monitoring the formation of amplification product involves the continuous measurement of PCR product accumulation using a dual-labeled nucleic acid probe, such as a hydrolysis probe. It will be appreciated that the invention is not limited to use of these probes and any tag-specific probe may be used.

In a fourth embodiment, the aliquots in the reaction chambers may be queried for the presence of the targeted nucleic acid analyte, which is accomplished by the use of the labeled probes. The fluorescent signal may be monitored and quantified with fluorescence detectors, such as fluorescence spectrophotometers and commercial systems that allow the monitoring of fluorescence in PCR reactions.

Alternatively, however, the probe may be unlabeled, but may be detectable by specific binding with a ligand which is labeled, either directly or indirectly. Suitable labels, and method for labeling probes and ligands are well known in the art, and include, for example, radioactive labels which may be incorporated by known methods (e.g., nick translation, random priming or kinasing), biotin, fluorescent groups, chemiluminescent groups (e.g., dioxetanes) enzymes, antibodies, gold nanoparticles and the like. Variations of this basic scheme are known in the art, and include those variations that facilitate separation of the hybrids to be detected from extraneous materials and/or that amplify the signal from the labeled moiety.

It will be appreciated that specifically at least about 10, more often at least about 25, still more often at least about 50, even more often at least about 100, in some cases at least about 500 and sometimes at least about 1000 targets may be detected using the methodology of the invention. Thus, the method may make use of at least about 10, more often at least about 25, still more often at least about 50, even more often at least about 100, in some cases at least about 500 and sometimes at least about 1000 target-specific probes.

All publications and patent documents (patents, published patent applications, and unpublished patent applications) cited herein are incorporated herein by reference as if each such publication or document was specifically and individually indicated to be incorporated herein by reference. Citation of publications and patent documents is not intended as an admission that any such document is pertinent prior art, nor does it constitute any admission as to the contents or date of the same.

While the exemplary embodiments have been described in some detail, by way of example and for clarity of understanding, those of skill in the art will recognize that a variety of modification, adaptations, and changes may be employed. Hence, the scope of the present invention should be limited solely by the claims.

What is claimed is:

1. A microfluidic device, comprising:
a first flow channel formed in a first layer of a substrate, the first flow channel is in fluid communication with a first chamber;
a first control channel formed in a second layer of a substrate, wherein the second layer is adjacent to the first layer; and
a second flow channel formed in a third layer of a substrate, wherein the third layer is adjacent to the second layer;
a reaction channel formed in the third layer, wherein the reaction channel is in fluid communication with the second flow channel, wherein a first portion of the reaction channel is in fluid communication with the first chamber, wherein a second portion of the reaction channel is in fluid communication with a second chamber, wherein an interface valve is disposed along the reaction channel to isolate the first portion from the second portion; and
a first isolation valve and a second isolation valve, each disposed along the first control channel, wherein a change in pressure within the first control channel actuates the first isolation valve to isolate the first chamber from a portion of the first flow channel and simultaneously actuates the second isolation valve to isolate the second portion of the reaction channel from the second flow channel.

2. The microfluidic device of claim 1, wherein the first isolation valve comprises a deflectable membrane.

3. The microfluidic device of claim 1, wherein the second isolation valve comprises a deflectable membrane.

4. The microfluidic device of claim 1, Wherein the first chamber disposed at least partially within the first layer.

5. The microfluidic device of claim 1, wherein the second chamber disposed at least partially within the first layer.

6. The microfluidic device of claim 1, wherein the substrate comprises an elastomeric material.

7. A microfluidic device, comprising:
a substrate having a first layer, a second layer, and a third layer, wherein the second layer is disposed between the first and third layers;
a first chamber formed at least partially within the first layer of the substrate;
a second chamber formed at least partially within the first layer of the substrate; and
a first control channel formed in the second layer of the substrate; and
a flow channel formed in the third layer;
a reaction channel formed in the third layer, wherein the reaction channel is in fluid communication with the flow channel, wherein a first portion of the reaction channel is in fluid communication with the first chamber, wherein a second portion of the reaction channel is in fluid communication with a second chamber, wherein an interface valve is disposed along the reaction channel to isolate the first portion from the second portion; and
a first isolation valve and a second isolation valve, each disposed along the first control channel,
wherein a change in pressure within the first control channel actuates the first isolation valve to modulate a first fluid flow passing through the first layer and into the first chamber, and also simultaneously actuates the second isolation valve to modulate a second fluid flow passing through the third layer and into the second chamber.

8. The microfluidic device of claim 7, wherein the interface valve is disposed along an interface channel that provides fluid communication between the first chamber and the second chamber.

9. The microfluidic device of claim 8, wherein the interface channel is formed in the third layer.

10. The microfluidic device of claim 7, wherein the interface valve comprises a deflectable membrane.

11. A microfluidic device, comprising:
a first flow channel formed in a first layer of a substrate;
a first chamber in fluid communication with the first flow channel;
a first isolation valve disposed along the first flow channel, wherein the first isolation valve comprises a first portion of a control channel formed in a second layer of the substrate adjacent to the first layer, and is configured to control flow through the first flow channel into the first chamber;
a second flow channel formed in a third layer of the substrate adjacent to the second layer;
a second chamber in fluid communication with the second flow channel;

a second isolation valve disposed along the second flow channel, wherein the second isolation valve comprises a second portion of the control channel formed in a second layer of the substrate, and is configured to control flow through the second flow channel into the second chamber;

a reaction channel formed in the third layer of the substrate, in fluid communication with the first chamber and the second chamber;

an interface valve disposed along the reaction channel between the first and second chamber, wherein the interface valve comprises a portion of an interface channel formed in a fourth layer of the substrate adjacent to the third layer, and is configured to control flow through the reaction channel.

12. The microfluidic device of claim 11, wherein the first isolation valve comprises a deflectable membrane.

13. The microfluidic device of claim 11, wherein the second isolation valve comprises a deflectable membrane.

14. The microfluidic device of claim 11, wherein the interface valve comprises a deflectable membrane.

15. The microfluidic device of claim 11, wherein the first chamber defines a first chamber volume, the second chamber defines a second chamber volume, and the first chamber volume is less than the second chamber volume.

16. The microfluidic device of claim 11, wherein the first chamber defines a first chamber volume within a range from about 0.1 nanoliters to about 10 nanoliters.

17. The microfluidic device of claim 11, wherein the reaction channel spans a distance between the first chamber and the second chamber, and the distance comprises a length within a range from about 200 µm to about 400 µm.

18. A microfluidic device, comprising:
a plurality of first flow channels formed in a first layer of a substrate;
a plurality of first chambers, wherein each one of the plurality of first chambers is in fluid communication with a corresponding first flow channel of the plurality of first flow channels;
a plurality of control channels formed in a second layer of the substrate adjacent to the first layer;
a plurality of first isolation valves, wherein each one of the plurality of first isolation valves is disposed along a corresponding first flow channel of the plurality of first flow channels, comprises a first portion of a corresponding control channel of the plurality of control channels, and is configured to control flow through the corresponding first flow channel into a corresponding first chamber of the plurality of first chambers;

a plurality of second flow channels formed in a third layer of the substrate adjacent to the second layer;
a plurality of second chambers, wherein each one of the plurality of second chambers is in fluid communication with a corresponding second flow channel of the plurality of second flow channels;
a plurality of second isolation valves, wherein each one of the plurality of second isolation valves is disposed along a corresponding second flow channel of the plurality of second flow channels, comprises a second portion of the corresponding control channel of the plurality of control channels, and is configured to control flow through the corresponding second flow channel into a corresponding second chamber of the plurality of second chambers;
a plurality of reaction channels formed in the third layer of the substrate, wherein each one of the plurality of reaction channels is in fluid communication with a corresponding first chamber of the plurality of first chambers and a corresponding second chamber of the plurality of second chambers;
a plurality of interface valves, wherein each one of the plurality of interface valves is disposed along a corresponding reaction channel of the plurality of reaction channels between the corresponding first chamber and the corresponding second chamber, comprises a portion of a corresponding interface channel of a plurality of interface channels formed in a fourth layer of the substrate adjacent to the third layer, and is configured to control flow through the corresponding reaction channel.

19. The microfluidic device of claim 1, wherein the first control channel modulates fluid flow within the first flow channel by deflecting a first membrane in a first direction into the first flow channel and modulates fluid flow within the second flow channel by deflecting a second membrane in a second direction into the second flow channel, wherein the first direction is opposite the second direction.

20. The microfluidic device of claim 1, wherein the first and second isolation valves are disposed at different positions horizontally along the first control channel.

21. The microfluidic device of claim 1, wherein height of the first chamber is greater than height the first flow channel.

22. The microfluidic device of claim 11, wherein the first and second isolation valves are disposed at different positions horizontally along the first control channel.

23. The microfluidic device of claim 11, wherein height of the first chamber is greater than height the first flow channel.

* * * * *